US008455456B2

(12) United States Patent
Yu et al.

(10) Patent No.: US 8,455,456 B2
(45) Date of Patent: *Jun. 4, 2013

(54) COMPOSITIONS AND THEIR USES DIRECTED TO DIACYLGLYCEROL ACYLTRANSFERASE 1

(75) Inventors: Xing-Xian Yu, San Diego, CA (US); Sanjay Bhanot, Carlsbad, CA (US); Brett P. Monia, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,457

(22) Filed: Jul. 6, 2011

(65) Prior Publication Data

US 2012/0029050 A1 Feb. 2, 2012

Related U.S. Application Data

(63) Continuation of application No. 11/834,640, filed on Aug. 6, 2007, now Pat. No. 8,003,620.

(60) Provisional application No. 60/821,511, filed on Aug. 5, 2006.

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl.
USPC ........ 514/44 A; 514/44 R; 435/375; 435/377; 536/23.1; 536/24.1; 536/24.5

(58) Field of Classification Search
None
See application file for complete search history.

(56) References Cited

U.S. PATENT DOCUMENTS

| | | | |
|---|---|---|---|
| 5,708,160 A | 1/1998 | Goh et al. |
| 5,801,154 A | 9/1998 | Baracchini et al. |
| 5,998,148 A | 12/1999 | Bennett et al. |
| 6,100,077 A | 8/2000 | Sturley et al. |
| 6,344,548 B1 | 2/2002 | Farese, Jr. et al. |
| 6,444,427 B1 | 9/2002 | Ludwig et al. |
| 6,512,099 B2 | 1/2003 | Omura et al. |
| 6,582,908 B2 | 6/2003 | Fodor et al. |
| 6,607,893 B2 | 8/2003 | Ramharack et al. |
| 6,822,141 B2 | 11/2004 | Lardizabal et al. |
| 6,867,039 B2 | 3/2005 | Monia et al. |
| 7,414,033 B2 | 8/2008 | Monia et al. |
| 7,745,691 B2 | 6/2010 | Farese et al. |
| 7,795,283 B2 | 9/2010 | Birch et al. |
| 2001/0053519 A1 | 12/2001 | Fodor et al. |
| 2002/0119138 A1 | 8/2002 | Cases et al. |
| 2002/0127627 A1 | 9/2002 | Ramharack et al. |
| 2002/0193315 A1 | 12/2002 | Omura et al. |
| 2003/0028923 A1 | 2/2003 | Lardizabal et al. |
| 2003/0073103 A1 | 4/2003 | Ludwig et al. |
| 2003/0100480 A1 | 5/2003 | Smith et al. |
| 2003/0104414 A1 | 6/2003 | Attersand |
| 2003/0115632 A1 | 6/2003 | Lardizabal et al. |
| 2003/0124126 A1 | 7/2003 | Cases et al. |
| 2003/0152574 A1 | 8/2003 | Logan et al. |
| 2003/0161831 A1 | 8/2003 | Cases et al. |
| 2003/0170691 A1 | 9/2003 | Gimeno et al. |
| 2003/0200563 A1 | 10/2003 | Butler et al. |
| 2003/0202968 A1 | 10/2003 | Cases et al. |
| 2003/0228597 A1 | 12/2003 | Cowsert et al. |
| 2004/0054177 A1 | 3/2004 | Otake et al. |
| 2004/0058820 A1 | 3/2004 | Hagmann et al. |
| 2004/0076977 A1 | 4/2004 | Georges et al. |
| 2004/0078836 A1 | 4/2004 | Farese et al. |
| 2004/0107459 A1 | 6/2004 | Lardizabal et al. |
| 2004/0122033 A1 | 6/2004 | Nargund et al. |
| 2004/0185559 A1 | 9/2004 | Monia et al. |
| 2007/0031844 A1 | 2/2007 | Khvorova et al. |

FOREIGN PATENT DOCUMENTS

| | | |
|---|---|---|
| EP | 1308459 | 5/2003 |
| WO | WO 99/67268 | 12/1999 |
| WO | WO 00/78961 | 12/2000 |
| WO | WO 01/68848 | 9/2001 |
| WO | WO 01/77389 | 10/2001 |
| WO | WO 02/08260 | 1/2002 |
| WO | WO 02/062954 | 8/2002 |
| WO | WO 02/086085 | 10/2002 |
| WO | WO 03/004630 | 1/2003 |

OTHER PUBLICATIONS

Branch et al., "A good antisense molecule is hard to find" TIBS (1998) 23:45-50.

Buhman et al., "DGAT1 is not essential for intestinal triacylglycerol absorption or chylomicron synthesis" J. Biol. Chem. (2002) 277:25474-25479.

Cases et al., "Identification of a gene encoding an acyl CoA: diacylglycerol acyltransferase, a key enzyme in triacylglycerol synthesis" PNAS (1998) 95:13018-13023.

Cases et al., "Cloning of DGAT2, a second mammalian diacylglycerol acyltransferase, and related family member" J. Biol. Chem. (2001) 276:38870-38876.

Chen et al., "Increased insulin and leptin sensitivity in mice lacking acyl CoA: diacylglycerol acyltransferase 1" J. Clin. Invest (2002) 109:1049-1055.

(Continued)

*Primary Examiner* — Sean McGarry

(74) *Attorney, Agent, or Firm* — Knobbe, Martens, Olson & Bear, LLP

(57) ABSTRACT

Disclosed herein are compounds, compositions and methods for modulating DGAT-1 activity. Preferably, the expression of DGAT-1 from a nucleic acid is inhibited. Methods are provided for treating, ameliorating or treating liver fibrosis, either directly or by treating an underlying etiological factor. Preferably, the treatment, amelioration or prevention comprises administering a DGAT-1 activity modulator.

24 Claims, 9 Drawing Sheets

OTHER PUBLICATIONS

Chen et al., "Leptin modulates the effects of acyl CoA: diacylglycerol acyltransferase deficiency on murine fur and sebaceous glands" J. Clin. Invest. (2002) 109:175-181.

Chen et al., "Inhibition of Triglyceride Synthesis as a Treatment Strategy for Obesity" Artherioscler. Thromb. Vasc. Biol. (2005) 25:482-486.

Cheng et al., "Human acyl-CoA: diacylglycerol acyltransferase is a tetrameric protein" Biochem. J. (2001) 359:707-714.

Chin, "On the Preparation and Utilization of Isolated and Purified Oligonucleotides" Document purportedly located on a CD-ROM and contributed to the public collection of the Katherine R. Everett Law Library of the University of North Caroline on Mar. 14, 2002.

Crooke et al., "Basic Principles of Antisense Therapeutics" Antisense Research and Application (1998) Chapter 1:1-50.

Farese et al., "Triglyceride synthesis: insights from the cloning of diacylglycerol acyltransferase" Curr. Opin. Lipidol. (2000) 11:229-234.

Lardizabal et al., "DGAT2 is a new diacylglycerol acyltransferase gene family: purification, cloning, and expression in insect cells of two polypeptides from *Mortierella ramanniana* with diacylglycerol acyltransferase activity" J. Biol. Chem. (2001) 276: 38862-38869.

Ludwig et al., "DGAT1 promoter polymorphism associated with alterations in body mass index, high density lipoprotein levels and blood pressure in Turkish women" Clin. Genet. (2002) 62:68-73.

Meegalla et al., "Concerted elevation of acyl-coenzyme A: diacylglycerol acyltransferase (DGAT) activity through independent stimulation of mRNA expression of DGAT1 and DGAT2 by carbohydrate and insulin" Biochem. Biophys. Res. Commun. (2002) 298:317-323.

Murray et al., "Inhibition of DGAT1 with a Novel Optimized Antisense Inhibitor Lowers Plasma Glucose Levels" Diabetes (2003) 52, A300:XP009077409.

New England Biolabs 1998/1999 Catalog, cover page, pp. 121 and 284.

Oelkers et al., "Characterization of two human genes encoded acyl coenzyme A: cholesterol acyltransferase-related enzymes" J. Biol. Chem. (1998) 273:26765-26771.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Smith et al., "Obesity resistance and multiple mechanisms of triglyceride synthesis in mice lacking DGAT" Nat. Genet. (2000) 25:87-90.

Tabata et al., "Xanthohumols, diacylglycerol acyltransferase inhibitors, from *Humulus lupulus*" Phytochemistry (1997) 46: 683-687.

Tomoda et al., "Roselipins, inhibitors of diacylglycerol acyltransferase, produced by *Gliocladium roseum* KF-1040" J. Antibiot. (1999) 52:689-694.

Waterman et al., "Distinct ontogenic patterns or overt and latent DGAT activities of rat liver microsomes" J. Lipid. Res. (2002) 43:1555-1562.

Yamaguchi et al., "DGAT1 ASO tratment reduces hepatic fibrosis without improving hepatic steatosis in DB/DB mice fed methionine choline deficient diets" Hepatology (2006) 44(4) Suppl. 1, p. 663A.

Yu et al., "Expression of either an antisense RNA or a dominant negative mutant of diacylglycerol acyltransferase (DGAT) blocks fat accumulation in insulin/dexamethasone induced 3T3-L1 cells" Circulation (1999) 100, 18 Supp.: 1.745.

Yu et al., "Posttranscriptional control of the expression and function of diacylglycerol acyltransferase-1 in mouse adipocytes" J. Biol. Chem. (2002) 277:50876-50884.

European Partial Search Report for Application # EP 04722144.5 dated Feb. 6, 2007.

European Partial Search Report for Application # EP 04722144.5 dated Jun. 22, 2007.

European Search Report for Application EP 07813825 dated Sep. 21, 2009.

International Search Report for Int. Application No. PCT/US04/06083 dated Jan. 24, 2006.

International Search Report for Int. Application No. PCT/US07/75297 dated Sep. 4, 2008.

Office Action for U.S. Appl. No. 10/803,482 dated Nov. 1, 2006.

Final Rejection for U.S. Appl. No. 10/803,482 dated Oct. 18, 2007.

Office Action for U.S. Appl. No. 12/173,744 dated Feb. 18, 2009.

Office Action for U.S. Appl. No. 11/834,640 dated Oct. 4, 2010.

Oil Red O staining (x100), 4 week

The expression of DGAT1, 2 and TNFa mRNA in db/db mice

COMPOSITIONS AND THEIR USES DIRECTED TO DIACYLGLYCEROL ACYLTRANSFERASE 1

CROSS-REFERENCE TO RELATED APPLICATIONS

This application is a continuation of U.S. application Ser. No. 11/834,640 filed Aug. 6, 2007, allowed Apr. 19, 2011, which claims the benefit of priority under 35 U.S.C. 119(e) to U.S. Provisional Application No. 60/821,511 filed Aug. 4, 2006, each of which is incorporated herein by reference in its entirety.

SEQUENCE LISTING

The present application is being filed along with a Sequence Listing in electronic format. The Sequence Listing is provided as a file entitled BIOL0088USC1SEQ.txt, created on Jul. 1, 2011 which is 72 Kb in size. The information in the electronic format of the sequence listing is incorporated herein by reference in its entirety.

BACKGROUND OF THE INVENTION

Dysregulation of diacylglycerol acyltransferase 1 may play a role in the development of obesity. Upon differentiation of mouse 3T3-L1 cells into mature adipocytes, a 90 fold increase in diacylglycerol acyltransferase 1 levels is observed. However, forced overexpression of diacylglycerol acyltransferase 1 in mature adipocytes results in only a 2 fold increase in diacylglycerol acyltransferase 1 levels. This leads to an increase in cellular triglyceride synthesis without a concomitant increase in triglyceride lipolysis, suggesting that manipulation of the steady state level of diacylglycerol acyltransferase 1 may offer a potential means to treat obesity (Yu et al., *J. Biol. Chem.*, 277, 50876-50884 (2002)).

In a random Turkish population, five polymorphisms in the human diacylglycerol acyltransferase 1 promoter and 5' non-coding sequence have been identified. One common variant, C79T, revealed reduced promoter activity for the 79T allele and is associated with a lower body mass index, higher plasma cholesterol HDL levels, and lower diastolic blood pressure in Turkish women (Ludwig et al., *Clin. Genet.*, 62, 68-73 (2002)).

Diacylglycerol acyltransferase 1 knockout mice exhibit interesting phenotypes which indicate inhibition of diacylglycerol acyltransferase as a potential treatment for obesity and obesity-associated insulin resistance. Mice lacking diacylglycerol acyltransferase 1 are viable and can still synthesize triglycerides through other biological routes. However the mice are lean and resistant to diet-induce obesity (Smith et al., *Nat. Genet.*, 25, 87-90 (2000)), have decreased levels of tissue triglycerides, and increased sensitivity to insulin and leptin (Chen et al., *J. Clin. Invest.*, 109, 1049-1055 (2002)). Small molecule approaches to modulating the synthesis of diacylglycerol acyltransferase 1 are ineffective. (Tabata et al., *Phytochemistry*, 46, 683-687 (1997); Tomoda et al., *J. Antibiot.* (Tokyo), 52, 689-694 (1999)).

Diacylglycerol transferase 2 possesses diacylglycerol transferase activity that utilizes a broad range of long chain fatty acyl-CoA substrates (Cases et al., *J. Biol. Chem.*, 276, 38870-38876 (2001); Lardizabal et al., *J. Biol. Chem.*, 276, 38862-38869 (2001)). Diacylglycerol transferase 2 is a member of a family of genes whose sequences are unrelated to diacylglycerol acyltransferase 1. (Cases et al., *J. Biol. Chem.*, 276, 38870-38876 (2001)).

Diacylglycerol transferase 2 mRNA is preferentially upregulated by insulin treatment, as shown by in vitro assays measuring the diacylglycerol activity from the membrane fraction of cultured mouse adipocytes. In fasting mice, diacylglycerol transferase 2 expression is greatly reduced, and dramatically increases upon refeeding. The expression patterns of two enzymes that participate in fatty acid synthesis, acetyl-CoA carboxylase and fatty acid synthase, respond to fasting and refeeding in a similar fashion. These results, combined with the observation that diacylglycerol transferase 2 is abundantly expressed in liver, suggest that diacylglycerol transferase 2 is tightly linked to the endogenous fatty acid synthesis pathway (Meegalla et al., *Biochem. Biophys. Res. Commun.*, 298, 317-323 (2002)).

Studies of mice harboring a disruption in the diacylglycerol acyltransferase 1 gene provide evidence that diacylglycerol acyltransferase 2 contributes to triglyceride synthesis. Levels of diacylglycerol transferase 2 mRNA expression are similar in intestinal segments from both wild type and diacylglycerol transferase 1-deficient mice. Using magnesium chloride to distinguish between diacylglycerol transferase 1 and 2 activity, Buhman, et al. observed that, in diacylglycerol transferase 1-deficient mice, diacylglycerol transferase activity is reduced to 50% in the proximal intestine and to 10-15% in the distal intestine (Buhman et al., *J. Biol. Chem.*, 277, 25474-25479 (2002)).

Additionally, diacylglycerol transferase 2 mRNA levels are not up-regulated in the liver or adipose tissues of diacylglycerol transferase 1-deficient mice, even after weeks of high-fat diet. However, in ob/ob mice, which have a mutation in the leptin gene that results in obesity, diacylglycerol transferase 2 is more highly expressed than in wild type mice, suggesting that diacylglycerol transferase 2 may be partly responsible for the highly accumulated fat mass seen in these mice. Furthermore, the combined mutations of leptin and diacylglycerol transferase 1 leads to a three-fold elevation in diacylglycerol transferase 2 expression in white adipose tissue, compared to the levels in the same tissue from diacylglycerol transferase 1-deficient mice. These data suggest leptin normally down-regulates diacylglycerol transferase 2 expression, and that the upregulation of diacylglycerol transferase 2 in white adipose tissue in these mice may provide an alternate pathway for the triglyceride synthesis that still occurs in leptin deficient/diacylglycerol transferase 1-deficient mice (Chen et al., *J. Clin. Invest.*, 109, 1049-1055 (2002); Cases et al., *J. Biol. Chem.*, 276, 38870-38876 (2001); Chen et al., *J. Clin. Invest.*, 109, 175-181 (2002)).

Liver fibrosis is the excessive accumulation of extracellular matrix proteins that occurs in many types of chronic liver diseases. Advanced liver fibrosis results in complications such as cirrhosis, liver failure and portal hypertension; frequently requiring a liver transplant. Common causes of liver fibrosis include chronic hepatitis C infection, alcohol abuse and non-alcoholic steatohepatitis (NASH). NASH is characterized by obesity, type-2 diabetes mellitus, dislypidemia and, commonly, insulin resistance. Cellular mechanisms of liver fibrosis include the release of soluable factors from kupfer cells that will activate hepatic stellate cells (HSC) into fibrogenic myoblasts. Active HSC further secrete cytokines to perpetuate the active state. Following persistant injury, the active HSC produce large amounts of extracellular matrix proteins (ECM). Degradation of the ECM is prevented by the actions of cytokines, such as TIMPs. Currently, there is no standard therapy for liver fibrosis. As such, the recommended course of action is to remove the causative agent, which for NASH would include weight loss and specific treatments for metabolic syndrome. (See e.g., Battler, R. and Brenner, D. A., J. Clin. Invest. 115:209-218 (2005) and supplement; Elsharkawy, A. M., Oakley, F. and Mann, D. A., *Apoptosis v.* 10, n. 4, 927-939 (2005); and Rockey, D. C. *Clinincal Gastroenterology and Hepatology* 3:95-107 (2005)).

There is a recognized need in the art for a treatment for liver fibrosis.

SUMMARY OF THE INVENTION

Provided herein are compounds, particularly oligomeric compounds, especially nucleic acid and nucleic acid-like oligomers, which are targeted to a nucleic acid encoding Diacylglycerol Acyltransferase 1 (hereinafter "DGAT-1"). Preferably, the oligomeric compounds are antisense oligonucleotides targeted to a nucleic acid that encodes a DGAT-1 polypeptide, particularly human DGAT-1, that modulate the expression of DGAT-1. Preferably, the nucleic acid that encodes DGAT-1 has a nucleic acid sequence that is substantially similar to GenBank Accession No. NM_012079.2, entered Apr. 1, 2000 (SEQ ID NO: 4); incorporated herein by reference. More preferably, the nucleic acid is SEQ ID NO: 4. The oligomeric compounds comprise at least an 8 nucleoside portion, preferably a 12 nucleoside portion, more preferably at least a 15 nucleoside portion, of the sequences listed in Table 3, 4 or 6, or are at least 80% identical to validated target segments, or the sequences listed in or below Table 3, 4, or 6.

Methods are provided for modulating the activity of DGAT-1 in cells or tissues. Preferably, the activity of DGAT-1 is modulated by a compound that is specific for DGAT-1. More preferably, the specific DGAT activity modulator is an antisense compound that targets a nucleic acid that expresses DGAT-1 polypeptide. DGAT-1 activity is modulated in cells or tissues by contacting said cell or tissue with said modulator. DGAT-1 activity is modulated in an animal needing such modulation by administering the compound to said animal. Preferably, the modulator is administered as a pharmaceutically acceptable salt. The animal in need is suffering from liver fibrosis.

Methods are also provided for modulating the expression of DGAT-1 in cells or tissues comprising contacting the cells with at least one DGAT-1 modulating compound and analyzing the cells for indicators of a decrease in expression of DGAT-1 mRNA and/or protein by direct measurement of mRNA and/or protein levels, and/or indicators of liver fibrosis.

Further provided are methods for the prevention, amelioration, and/or treatment of liver fibrosis, increased collagen deposition in the liver, elevated levels of a-SMA mRNA levels, elevated TGF.beta. mRNA levels, elevated hydroxylproline, reduced retinol esterification in the liver, increased hepatic stellate cell activation and other indicators and endpoints of liver fibrosis comprising administering a DGAT-1 modulator to an individual in need of such intervention.

Further provided are methods of for the prevention, amelioration, and/or treatment of liver fibrosis by treating a causative agent, wherein the causative agent is treated by modulating DGAT-1 expression. The causative agent preferably being elevated plasma triglyceride levels, elevated liver triglyceride levels, liver statosis, NASH, NAFLD, obesity, diabetes mellitus, dyslipidemia, insulin resistance, metabolic syndrome, cholesterolemia or combinations thereof.

Provided are methods of use of a DGAT-1 modulator the preparation of a medicament for the prevention, amelioration or treatment of a disease, especially a disease associated with and including at least one indicator of liver fibrosis.

DETAILED DESCRIPTION OF THE INVENTION

Figure 1:
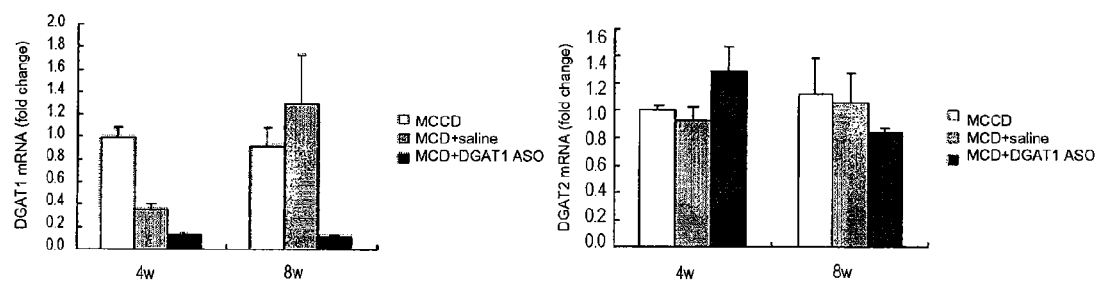
FIG. 1 is a series of graphs of DGAT-1 mRNA expression and DGAT-2 mRNA expression from liver tissue of mice either in the control groups (normal chow), the placebo group (MCD diet and saline) or the treatment group (MCD diet and DGAT-1 ASO treatment). Results are 4 week and 8 week.

Liver fibrosis is major health problems arising from chronic liver injury by a variety of etiological factors, including virus, alcohol abuse and components of the metabolic syndrome. (Elsharkawy, A. M. and Mann, D. A., *Apoptosis, v.* 10, n. 4 (2005) Therapeutic interventions for these diseases or conditions are not satisfactory. (See e.g., Battler, R. and Brenner, D. A., *J. Clin. Invest.* 115:209-218 (2005) and supplement; Elsharkaway, A. M., Oakley, F. and Mann, D. A., Apoptosis v. 10, n. 4, 927-939 (2005); and Rockey, D. C. *Clinincal Gastroenterology and Hepatology* 3:95-107 (2005)). Provided herein are compounds and methods for the prevention, amelioration, and/or treatment of liver fibrosis and etiological factors leading thereto.

As used herein, the term "prevention" means to delay or forestall onset or development of a condition or disease for a period of time from hours to days, preferably weeks to months. As used herein, the term "amelioration" means a lessening of at least one indicator of the severity of a condition or disease. The severity of indicators may be determined by subjective or objective measures which are known to those skilled in the art. As used herein, "treatment" means to administer a composition of the invention to effect an alteration or improvement of the disease or condition.

Disclosed herein are antisense compounds, including antisense oligonucleotides and other antisense compounds for use in modulating the expression of nucleic acid molecules encoding DGAT-1. This is accomplished by providing antisense compounds that hybridize with one or more target nucleic acid molecules encoding DGAT-1. As used herein, the terms "target nucleic acid" and "nucleic acid molecule encoding DGAT-1" have been used for convenience to encompass RNA (including pre-mRNA and mRNA or portions thereof) transcribed from DNA encoding DGAT-1, and also cDNA derived from such RNA. In a preferred embodiment, the target nucleic acid is an mRNA encoding DGAT-1.

Target Nucleic Acids

"Targeting" an antisense compound to a particular target nucleic acid molecule can be a multistep process. The process usually begins with the identification of a target nucleic acid whose expression is to be modulated. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes DGAT-1. "Target site" refers to the 5' most nucleoside on a target nucleic acid that hybridizes with an oligomer compound. The target site is calculated based upon the design of the oligomeric compound with respect to the sequence of the target nucleic acid.

Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease. Antisense compounds targeted to such variants are within the scope of the instant invention.

Target Names, Synonyms, Features

Herein are compositions and methods for modulating the activity of DGAT-1 (Diacylglycerol O-acyltransferase, ACAT related gene product 1; ARGP1; Acyl-CoA:diacylglycerol acyltransferase; DGAT; DGAT1; acyl coenzyme A:cholesterol acyltransferase related gene 1; diacylglycerol acyltransferase; diglyceride acyltransferase) In a preferred embodiment, these compositions and methods modulate the expression of a nucleic acid molecule that encodes a DGAT-1 polypeptide. Table 1 lists the GenBank accession numbers of sequences corresponding to nucleic acid molecules encoding DGAT-1 (nt=nucleotide), the date the version of the sequence was entered in GenBank, and the corresponding SEQ ID NO in the instant application, when assigned, each of which is incorporated herein by reference. Preferably, the compositions and methods modulate the expression of DGAT-1 polypeptide from a nucleic acid molecule that comprises a sequence that is substantially similar to SEQ ID NO: 4. The phrase "substantially similar" means that a relevant sequence is at least 70%, 75%, 80%, 85%, 90%, 92%, 95% 96%, 97%, 98%, or 99% identical to a given sequence. Without providing an exhaustive list of percentages, the use of at least in this context means that the similarity between the sequences ambraces the recited number and all calculations of idenity greater than, including whole and partial numbers. For example, at least 70% includes all whole numbers and all decimal numbers from 70% to 99.9%. By way of example only, a relevant sequence and a given sequence both being 300 consecutive nucleosides in length, but sharing identity between only 278 nucleosides would be 92.6% identical. One ordinarily skilled in the art will readily determine these percentages. Percent identity between two sequences can be determined by standard alignment algorithms such as ClustalX when the two sequences are in best alignment according to the alignment algorithm. Most preferably, the compositions and methods modulate the expression of DGAT-1 polypeptide from a nucleic acid molecule that is SEQ ID NO: 4.

TABLE 1

Gene Targets

| Species | Genbank # | Genbank Date | SEQ ID NO |
|---------|-----------|--------------|-----------|
| human | BQ084235.1 | Apr. 4, 2002 | 1 |
| human | AW391923.1_COMP | Feb. 4, 2000 | 2 |
| human | NT_031818.5_TRUNC_226000_247000_COMP | Aug. 1, 2002* | 3 |
| human | NM_012079.2 | Apr. 1, 2000 | 4 |
| human | BI907285.1 | Oct. 16, 2001 | 5 |
| human | BQ225153.1 | May 2, 2002 | 6 |
| mouse | AF078752.1 | Nov. 12, 1998 | 7 |
| mouse | AI448840.1_COMP | Feb. 26, 1999 | 8 |
| mouse | NM_010046.2 | Jun. 19, 2003 | 9 |

*replaced by NT_037704

Modulation

"Modulation" means that the activity of a compound is altered. Modulation of DGAT-1, for example, means that the activity of DGAT-1 is altered either through direct modulation of the DGAT-1 polypeptide, through the modulation of its expression from DNA or mRNA, or a combination thereof. Direct modulation of DGAT-1 can include small molecules, polypeptides, polynucleic acids, antibodies or other compounds that interact with the DGAT-1 polypeptide to modulate (increase or decrease) the activity of that polypeptide. Modulation of expression of a target nucleic acid can be achieved through alteration of any number of nucleic acid (DNA or RNA) functions. For example, and with respect to modulation of mRNA expression, modulation means either an increase (stimulation or induction) or a decrease (inhibition or reduction) in expression of the DGAT-1 polypeptide from the nucleic acid. As another example, modulation of expression can include perturbing splice site selection of pre-mRNA processing. "Expression" includes all the functions by which a gene's coded information is converted into structures present and operating in a cell. These structures include the products of transcription and translation. Modulation of expression means the perturbation of such functions. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of DGAT-1. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of antisense compounds of the present invention on target nucleic acid expression can be tested in any of a variety of cell types provided that the target nucleic acid is present at measurable levels. The effect of antisense compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and other public sources, and are well known to those skilled in the art. Primary cells, or those cells which are isolated from an animal and not subjected to continuous culture, can be prepared according to methods known in the art, or obtained from various commercial suppliers. Additionally, primary cells include those obtained from donor human subjects in a clinical setting (i.e. blood donors, surgical patients). Primary cells prepared by methods known in the art.

Assaying Modulation of DGAT-1

Modulation of DGAT-1 expression can be assayed in a variety of ways known in the art. DGAT-1 mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant invention.

Levels of a protein encoded by DGAT-1 can be quantitated in a variety of ways well known in the art, such as immunoprecipitation, Western blot analysis (immunoblotting), ELISA or fluorescence-activated cell sorting (FACS). Antibodies directed to a protein encoded by DGAT-1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997.

Active Target Segments

The locations on the target nucleic acid defined by having one or more active antisense compounds targeted thereto are referred to as "active target segments." When an active target segment is defined by multiple antisense compounds, the compounds are preferably separated by no more than about 10 nucleotides on the target sequence, more preferably no more than about 5 nucleotides on the target sequence, even more preferably the compounds are contiguous, most preferably the compounds are overlapping. There may be substantial variation in activity (e.g., as defined by percent inhibition) of the antisense compounds within an active target segment. Active antisense compounds are those that modulate the expression of their target RNA. Active antisense compounds inhibit expression of their target RNA by at least 45%, preferably at least 50%, more preferably at least 70%, more preferably still at least 80%, more preferably still at least 90%, and most preferably at least 95%. As stated above, at least is used to include the recited number and all whole and decimal numbers greater than. In a more preferred embodiment, the level of inhibition required to define an active antisense compound is defined based on the results from the screen used to define the active target segments.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural base 5-methyl cytosine and the artificial base known as a G-clamp. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize toa target sequence are determined by the nature and composition of the antisense compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid.

Identity

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences of the instant invention would be considered identical as they both pair with adenine. Similarly, a G-clamp modified heterocyclic base would be considered identical to a cytosine or a 5-Me cytosine in the sequences of the instant application as it pairs with a guanine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of the invention. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). In a preferred embodiment, antisense compounds will have no more that three mismatches to a nucleic acid sequence encoding DGAT-1. The term "no more that three mismatches" embraces 0 mismatches, 1 mismatch, 2 mismatches and 3 mismatches. Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art, and furthermore, those skilled in the art readily recognize that calculations of percent identity may equate to non-whole number percentages.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. In the context of the invention, the complement of an active target segment may constitute a single portion. In a preferred embodiment, the oligonucleotides of the instant invention are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA in an oocyte injection model. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358, 1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs.

Therapeutics

The antisense compounds can be used to modulate the expression of DGAT-1 in an animal, such as a human. In one non-limiting embodiment, the methods comprise the step of administering to said animal in need of therapy for a disease or condition associated with DGAT-1 an effective amount of an antisense compound that inhibits expression of DGAT-1. A disease or condition associated with DGAT-1 includes, but is not limited to, liver fibrosis. In one embodiment, the antisense compounds of the present invention effectively inhibit the levels or function of DGAT-1 RNA. Because reduction in DGAT-1 mRNA levels can lead to alteration in DGAT-1 protein products of expression as well, such resultant alterations can also be measured. Antisense compounds of the present invention that effectively inhibit the level or function of DGAT-1 RNA or protein products of expression are considered an active antisense compounds. In one embodiment, the antisense compounds inhibit the expression of DGAT-1 causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of DGAT-1 can be measured in a bodily fluid, tissue or organ of the animal. Methods of obtaining samples for analysis, such as body fluids (e.g., blood), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the DGAT-1 expression in the aforementioned fluids, tissues or organs, collected from an animal contacted with one or more compounds of the invention, by routine clinical methods known in the art. These biomarkers include but are not limited to: liver transaminases, bilirubin, albumin, blood urea nitrogen, creatine and other markers of kidney and liver function; interleukins, tumor necrosis factors, intracellular adhesion molecules, C-reactive protein, chemokines, cytokines, and other markers of liver fibrosis, obesity, liver statosis, NASH, NAFLD, diabetes mellitus, dyslipidemia, insulin resistance, metabolic syndrome or cholesterolemia.

The antisense compounds of the present invention can be utilized in pharmaceutical compositions by adding an effective amount of a compound to a suitable pharmaceutically acceptable diluent or carrier. Acceptable carriers and dilutents are well known to those skilled in the art. Selection of a dilutent or carrier is based on a number of factors, including, but not limited to, the solubility of the compound and the route of administration. Such considerations are well understood by those skilled in the art. In one aspect, the compounds of the present invention inhibit the expression of DGAT-1. The compounds of the invention can also be used in the manufacture of a medicament for the treatment of diseases and disorders related to DGAT-1 expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of DGAT-1 expression in the cells of bodily fluids, organs or tissues.

Thus, provided herein is the use of a modulator of DGAT-1, preferably an isolated single- or double-stranded antisense compound targeted to DGAT-1, in the manufacture of a medicament for the treatment of a disease or disorder by means of the method described above. In a more preferred embodiment, the antisense compound is a single stranded antisense compound. In a most preferred embodiment, the compound is a chimeric antisense compound comprising a consecutive nucleoside length range, wherein the upper end of the range is 50 nucleosides and wherein the lower end on the range is 12 nucleosides, further comprising one or more of a nucleobase modification, an internucleoside linkage modification, a high-affinity sugar modification or a combination thereof, and further comprising no more than three mismatches to a target nucleic acid sequence that encodes DGAT-1.

Kits, Research Reagents, and Diagnostics

The antisense compounds of the present invention can be utilized for diagnostics, and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the antisense compounds of the present invention, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Compounds

The term "oligomeric compound" refers to a polymeric structure capable of hybridizing to a region of a nucleic acid molecule. Generally, oligomeric compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar includes a nucleobase, modified nucleobase or a nucleobase mimetic. Preferred monomeric subunits comprise nucleosides and modified nucleosides.

An "antisense compound" or "antisense oligomeric compound" refers to an oligomeric compound that is at least partially complementary to the region of a target nucleic acid molecule to which it hybridizes and which modulates (increases or decreases) its expression. This term includes oligonucleotides, oligonucleotides, oligonucleotide analogs, oligonucleotide mimetics, antisense compounds, antisense oligomeric compounds, and chimeric combinations of these. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Antisense double-stranded compounds can be two strands hybridized to form double-stranded compounds or a single strand with sufficient self complementarity to allow for hybridization and formation of a fully or partially double-stranded compound. The compounds of the instant invention are not auto-catalytic. As used herein, "auto-catalytic" means a compound has the ability to promote cleavage of the target RNA in the absence of accessory factors, e.g. proteins.

In one embodiment, the antisense compound comprises a single stranded oligonucleotide. In some embodiments of the invention the antisense compound contains chemical modifications. In a preferred embodiment, the antisense compound is a single stranded, chimeric oligonucleotide wherein the modifications of sugars, bases, and internucleoside linkages are independently selected. In a more preferred embodiment the compound is a chimeric antisense compound comprising a consecutive nucleoside length range, wherein the upper end of the range is 50 nucleosides and wherein the lower end on the range is 12 nucleosides, further comprising one or more of a nucleobase modification, an internucleoside linkage modification, a high-affinity sugar modification or a combination thereof, and further comprising no more than three mismatches to the target nucleic acid sequence (SEQ ID NO: 4) that encodes DGAT-1.

The antisense compounds herein may comprise a consecutive nucleoside length range, wherein the upper end of the range is 50 nucleosides and wherein the lower end on the range is 12 nucleosides. More preferably, the upper end of the range is 35 nucleosides and the lower end of the range is 14 nucleosides. More preferably still the upper end of the range is 24 nucleosides and the lower end of the range is 17 nucleosides. Most preferably the antisense compound is 20 consecutive nucleosides. Those skilled in the art will readily recognize that the upper end of the range, as disclosed herein comprises 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive nucleosides and the lower end of the range comprises 12, 13, 14, 15, 16, 17, 18, 19 or 20 consecutive nucleosides.

Antisense compounds, as disclosed herein, also comprise a stretch of at least 8, preferably at least 12, more preferably at least 15 consecutive nucleosides selected from within the active target regions are considered to be suitable antisense compounds as well.

Modifications can be made to the antisense compounds of the instant invention and may include conjugate groups attached to one of the termini, selected nucleobase positions, sugar positions or to one of the internucleoside linkages. Possible modifications include, but are not limited to, 2'-fluoro (2'-F), 2'-O-Methyl (2'-OMe), 2'-O-(2-methoxyethyl)(2'-MOE) high affinity sugar modifications, inverted abasic caps, deoxynucleobases, and bicyclice nucleobase analogs such as locked nucleic acids (LNA) and ethylene-bridged nucleic acids (ENA).

In one embodiment of the invention, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleosides to form an overhang.

Each strand of the siRNA duplex may fall within the length ranges disclosed above. In a preferred embodiment, each strand of the siRNA duplex is about 17 to about 25 nucleosides. The two strands may be fully complementary (i.e., form a blunt ended compound), or include a 5' or 3' overhang on one or both strands. Double-stranded compounds can be made to include chemical modifications as discussed herein.

Chemical Modifications

As is known in the art, and as referred to herein, the term "nucleoside" is used to refer to a base-sugar combination of a nucleic acid monomer unit. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the present invention. The terms modified nucleobase and nucleobase mimetic can overlap but generally a modified nucleobase refers to a nucleobase that is fairly similar in structure to the parent nucleobase, such as for example a 7-deaza purine or a 5-methyl cytosine, whereas a nucleobase mimetic would include more complicated structures, such as for example a tricyclic phenoxazine nucleobase mimetic. Methods for preparation of the above noted modified nucleobases are well known to those skilled in the art.

Antisense compounds of the present invention may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-($CH_2$)$_2$—O-2' bridge); and substituted sugars, especially 2'-substituted sugars having a 2'-F, 2'-OCH$_2$ or a 2'-O($CH_2$)$_2$—OCH$_3$ substituent group. Sugars can also be replaced with sugar mimetic groups among others. Methods for the preparations of modified sugars are well known to those skilled in the art.

Internucleoside linking groups link the nucleosides or otherwise modified monomer units together, thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

In the context of this invention, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

The present invention provides compounds having reactive phosphorus groups useful for forming internucleoside linkages including for example phosphodiester and phosphorothioate internucleoside linkages. Methods of preparation and/or purification of precursors or antisense compounds of the instant invention are not a limitation of the compositions or methods of the invention. Methods for synthesis and purification of DNA, RNA, and the antisense compounds of the instant invention are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound of the present invention.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric oligomeric compounds can be further described as having a particular motif. As used in the present invention the term "motif" refers to the orientation of modified sugar moieties and/or sugar mimetic groups in an antisense compound relative to like or differentially modified or unmodified nucleosides. As used in the present invention, the terms "sugars", "sugar moieties" and "sugar mimetic groups" are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an antisense compound.

As used in the present invention the term "gapped motif" refers to an antisense compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The nucleosides located in the gap of a gapped antisense compound have sugar moieties that are different than the modified sugar moieties in each of the wings. By way of example only, and not limitation, an antisense compound that is 20 nucleobases in length comprising five consecutive 2'-O-(2-methoxyethyl) sugar modifications at the 5' end of the compound, followed by ten consecutive 2' deoxy sugars which are followed by five consecutive 2'-O-(2-methoxyethyl) sugar modifications at the 3' end of the compound. This motif represents a 2' deoxy gap flanked by 2'-O-(2-methoxyethyl) wings. In a further non-limiting example, an antisense compound is 14 nucleobases in length comprising three consecutive 2'-O-(2-methoxyethyl) sugar modifications at the 5' end of the compound, followed by eight consecutive 2' deoxy sugars which are followed by three consecutive 2'-O-(2-methoxyethyl) sugar modifications at the 3' end of the compound. This motif also represents a 2' deoxy gap flanked by 2'-O-(2-methoxyethyl) wings.

As used in the present invention the term "alternating motif" refers to an antisense compound comprising a contiguous sequence of nucleosides comprising two differentially sugar modified nucleosides that alternate for essentially the entire sequence of the antisense compound, or for essentially the entire sequence of a region of an antisense compound.

As used in the present invention the term "fully modified motif" refers to an antisense compound comprising a contiguous sequence of nucleosides wherein essentially each nucleoside is a sugar modified nucleoside having uniform modification.

As used in the present invention the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound.

As used in the present invention the term "blockmer motif" refers to a sequence of nucleosides that have uniform sugars (identical sugars, modified or unmodified) that is internally interrupted by a block of sugar modified nucleosides that are unifoHnly modified and wherein the modification is different from the other nucleosides. Methods of preparation of chimeric oligonucleotide compounds are well known to those skilled in the art.

As used in the present invention the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), α or β, or as (D) or (L) such as for amino acids et al. The present invention is meant to include all such possible isomers, as well as their racemic and optically pure forms.

In one aspect of the present invention antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Salts, Prodrugs and Bioequivalents

Compounds may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs comprising the antisense compounds, which may further comprise, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the compounds are prepared as SATE ((S-acetyl-2-thioethyl) phosphate) derivatives according to the methods disclosed in WO 93/24510 or WO 94/26764. Prodrugs can include antisense compounds wherein one or both ends comprise nucleosides that are cleaved (e.g., phosphodiester backbone linkages) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. By example only, sodium salts of antisense oligonucleotides are useful and are well accepted for therapeutic administration to humans. In another embodiment, sodium salts of dsRNA compounds are also provided.

Formulations

The compounds may also be admixed, encapsulated, conjugated or otherwise associated with other molecules, molecule structures or mixtures of compounds. In a preferred embodiment, the pharmaceutical compositions comprise a compound that modulated DGAT-1 activity. More preferably, the compound is a specific inhibitor of DGAT-1 activity. More preferably, the compound is an antisense compound. The pharmaceutical compositions may be administered in a number of ways depending upon whether local or systemic treatment is desired and upon the area to be treated.

Pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery).

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions can contain two or more compounds. In a preferred embodiment, the two or more compounds are modulators of DGAT-1 activity. In a further preferred embodiment, the two or more compounds are useful for treating liver fibrosis, either directly or by treating a causative etiological factor. In another related embodiment, compositions can contain one or more antisense compounds, particularly oligonucleotides, targeted to a first nucleic acid and one or more additional antisense compounds targeted to a second nucleic acid target. In one aspect of this embodiment, the first nucleic acid targeted is DGAT-1 and the second nucleic acid targeted is associated with an underlying etiological factor for liver fibrosis; for example DGAT-2. DGAT-2 has been disclosed as a treatment for obesity, diabetes, liver steatosis, cholesterolemia and other similar indications. (U.S. Published App. No.: US2005-0272680). Alternatively, compositions can contain two or more antisense compounds targeted to different regions of the same nucleic acid target. Two or more combined compounds may be used together or sequentially.

Nonlimiting Disclosure and Incorporation by Reference

While certain compounds, compositions and methods of the present invention have been described with specificity in accordance with certain embodiments, the following examples serve only to illustrate the compounds of the invention and are not intended to limit the same. Each of the references, GenBank accession numbers, and the like recited in the present application is incorporated herein by reference in its entirety.

EXAMPLE 1

Cell Types and Transfection Methods

Cell types—The effect of oligomeric compounds on target nucleic acid expression was tested in one or more of the following cell types.

HepG2 cells: The human hepatoblastoma cell line HepG2 was obtained from the American Type Culture Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

b.END cells: The mouse brain endothelial cell line b.END was obtained from Dr. Werner Risau at the Max Plank Institute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analysis, cells may be seeded onto 100 mm or other standard tissue culture plates and treated similarly, using appropriate volumes of medium and oligonucleotide.

Treatment with oligomeric compounds: When cells reach appropriate confluency, they are treated with oligonucleotide using a transfection method as described.

Lipofectin™ When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture was incubated at room temperature for approximately 0.5 hours. For cells grown in 96-well plates, wells were washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

Control Oligonucleotides

Control oligonucleotides are used to determine the optimal oligomeric compound concentration for a particular cell line. Furthermore, when oligomeric compounds of the invention are tested in oligomeric compound screening experiments or phenotypic assays, control oligonucleotides are tested in parallel with compounds of the invention.

The concentration of oligonucleotide used varies from cell line to cell line. To determine the optimal oligonucleotide concentration for a particular cell line, the cells are treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 1 µM to 40 µM when the antisense oligonucleotide is transfected by electroporation.

For human cells the positive control oligonucleotide is selected from either Oligo 13920 (TCCGTCATCGCTCCTCAGGG, SEQ ID NO: 10) which is targeted to human H-ras, or Oligo 18078, (GTGCGCGCGAGCCCGAAATC, SEQ ID NO: 11) which is targeted to human Jun-N-terminal kinase-2 (JNK2). Both controls are 2'-O-methoxyethyl gapmers (2'-O- methoxyethyls shown in bold) with a phosphorothioate backbone. For mouse or rat cells the positive control oligonucleotide is Oligo 15770 (ATGCATTCTGCCCCAAGGA, SEQ ID NO: 12).

EXAMPLE 2

Real-time Quantitative PCR Analysis of DGAT-1 mRNA Levels

Quantitation of DGAT-1 mRNA levels was accomplished by real-time quantitative PCR using the ABI PRISM™7600, 7700, or 7900 Sequence Detection System (PE-Applied Biosystems, Foster City, Calif.) according to manufacturer's instructions.

Prior to quantitative PCR analysis, primer-probe sets specific to the DGAT-1 being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 µL of RiboGreen™ working reagent (RiboGreen™ reagent diluted 1:350 in 10 mM Tris-HCl, 1 mM EDTA, pH 7.5) was pipetted into a 96-well plate containing 30 µL purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. The primers and probes and the target nucleic acid sequences to which they hybridize are presented in Table 2. The target-specific PCR probes have fluorescent dye and quencher dye covalently linked to the compounds.

TABLE 2

DGAT-1-specific primers and probes for use in real-time PCR

| Species | Target SEQ ID NO | Sequence Description | Sequence (5' to 3') | SEQ ID NO |
|---|---|---|---|---|
| Human |  | Fwd Primer | TCCCCGCATCCGGAA | 13 |
| Human |  | Rev Primer | CTGGGTGAAGAACAGCATCTCA | 14 |
| Human |  | Probe | FAM-CGCTTTCTGCTGCGACGGATCC-TAMRA | 15 |
| Mouse |  | Fwd Primer | GAAGGTGAAGGTCGGAGTC | 16 |
| Mouse |  | Rev Primer | GAAGATGGTGATGGGATTTC | 17 |
| Mouse |  | Probe | JOE-CAAGCTTCCCGTTCTCAGCC- TAMRA | 98 |

EXAMPLE 3

Antisense Inhibition of Human DGAT-1 Expression by Oligomeric Compounds

A series of antisense compounds was designed to target different regions of human DGAT-1 RNA, using published sequences or portions of published sequences as cited in Table 1. The screen identified active target segments within the human DGAT-1 mRNA sequence, specifically GenBank number (SEQ ID NO: 4). Compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytosine residues are 5-methyl cytosine. Data are averages from three experiments in which HepG2 cells were treated with 75 nM of the antisense oligonucleotides of the present invention.

TABLE 3

Inhibition of human DGAT-1 mRNA levels by chimeric phosphorothioate oligonucleotides having 2'-MOE wings and a deoxy gap

| CMPD # | REGION | TARGET SEQ ID NO | TARGET SITE | SEQUENCE | % INHIB | SEQ ID NO |
|---|---|---|---|---|---|---|
| 191617 | 5'UTR | 4 | 1 | gccgcctctctcgtccattc | 57 | 18 |
| 191619 | 5'UTR | 4 | 21 | gagccgctaactaatggacg | 37 | 19 |
| 191621 | 5'UTR | 4 | 41 | acaacggctgcgttgctccg | 30 | 20 |
| 191623 | 5'UTR | 4 | 71 | ccgcccgcgtcaggcccgtc | 40 | 21 |
| 191625 | 5'UTR | 4 | 91 | gcctcaccagcgcgttcaac | 20 | 22 |
| 191627 | 5'UTR | 4 | 120 | ccctgccggccgccgtagcc | 24 | 23 |
| 191629 | 5'UTR | 4 | 151 | ctccgggccctagacaacgg | 45 | 24 |
| 191631 | 5'UTR | 4 | 181 | gttcgtagcgcccgaggcgc | 53 | 25 |
| 191633 | 5'UTR | 4 | 211 | cccggccgcagccaagcgtg | 44 | 26 |
| 191635 | Start Codon | 4 | 231 | gcccatggcctcagcccgca | 77 | 27 |
| 191637 | Coding | 4 | 281 | tggctcgagggccgcgaccc | 58 | 28 |
| 191639 | Coding | 4 | 301 | ccgcaggcccgccgccgccg | 49 | 29 |
| 191641 | Coding | 4 | 321 | ccgcacctcttcttccgccg | 40 | 30 |
| 191643 | Coding | 4 | 401 | acgccggcgtctccgtcctt | 92 | 31 |
| 191645 | Coding | 4 | 421 | gctcccagtggccgctgccc | 60 | 32 |
| 191647 | Coding | 4 | 441 | ctgcaggcgatggcacctca | 85 | 33 |
| 191649 | Coding | 4 | 491 | aggatgccacggtagttgct | 62 | 34 |
| 191651 | Coding | 4 | 511 | gcatcaccacacaccagttc | 37 | 35 |
| 191653 | Coding | 4 | 561 | gccatacttgatgaggttct | 48 | 36 |
| 191655 | Coding | 4 | 651 | gacattggccgcaataacca | 47 | 37 |
| 191657 | Coding | 4 | 681 | cttctcaacctggaatgcag | 29 | 38 |
| 191659 | Coding | 4 | 721 | gcagtcccgcctgctccgtc | 50 | 39 |
| 191661 | Coding | 4 | 741 | caggttggctacgtgcagca | 31 | 40 |
| 191663 | Coding | 4 | 781 | ccagtaagaccacagccgct | 62 | 41 |
| 191665 | Coding | 4 | 831 | ggtgtgcgccatcagcgcca | 59 | 42 |
| 191667 | Coding | 4 | 931 | cagcactgctggccttcttc | 52 | 43 |
| 191669 | Coding | 4 | 1021 | tgagctcgtagcacaaggtg | 43 | 44 |
| 191671 | Coding | 4 | 1121 | cactgctggatcagccccac | 20 | 45 |
| 191673 | Coding | 4 | 1181 | atgcgtgagtagtccatgtc | 59 | 46 |
| 191675 | Coding | 4 | 1231 | tgagccagatgaggtgattg | 62 | 47 |
| 191677 | Coding | 4 | 1281 | gagctcagccacggcattca | 76 | 48 |
| 191679 | Coding | 4 | 1351 | tctgccagaagtaggtgaca | 30 | 49 |
| 191681 | Coding | 4 | 1611 | gatgagcgacagccacacag | 21 | 50 |
| 191683 | Coding | 4 | 1671 | ctcatagttgagcacgtagt | 73 | 51 |
| 191685 | 3'UTR | 4 | 1721 | cagtgagaagccaggccctc | 68 | 52 |
| 191687 | 3'UTR | 4 | 1781 | ccatccccagcactcgaggc | 68 | 53 |

TABLE 3-continued

Inhibition of human DGAT-1 mRNA levels by chimeric phosphorothioate oligonucleotides having 2'-MOE wings and a deoxy gap

| CMPD # | REGION | TARGET SEQ ID NO | TARGET SITE | SEQUENCE | % INHIB | SEQ ID NO |
|---|---|---|---|---|---|---|
| 191689 | 3'UTR | 4 | 1801 | aggatgctgtgcagccaggc | 73 | 54 |
| 191691 | 3'UTR | 4 | 1851 | ggtgcaggacagagccccat | 72 | 55 |
| 191693 | 3'UTR | 4 | 1881 | gtgtctggcctgctgtcgcc | 71 | 56 |
| 191695 | 3'UTR | 4 | 1901 | ctcccagctggcatcagact | 76 | 57 |

As shown in Table 3, SEQ ID Nos. 18, 25, 27, 28, 31, 32, 33, 34, 39, 41, 42, 43, 46, 47, 48, 51, 52, 53, 54, 55, 56 and 57 demonstrated at least 50% inhibition of human DGAT-1 expression in this assay and are therefore preferred. More preferred are SEQ ID NOs 31, 33, 27, and 57. The target regions to which these preferred sequences are complementary are herein referred to as "preferred target segments" and are therefore preferred for targeting by compounds of the present invention. These preferred target segments are shown in Table 3. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

EXAMPLE 4

Antisense Inhibition of Mouse DGAT-1 Expression by Chimeric Phosphorothioate Oligonucleotides Having 2'-MOE Wings and a Deoxy Gap In accordance with the present invention, a second series of antisense compounds was designed to target different regions of the mouse DGAT-1 RNA, using published sequences (GenBank accession number AF078752.1, incorporated herein as SEQ ID NO: 7). The compounds are shown in Table 4. "Target site" indicates the first (5'-most) nucleotide number on the particular target nucleic acid to which the compound binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytosine residues are 5-methyl cytosine. The compounds were analyzed for their effect on mouse DGAT-1 mRNA levels by quantitative real-time PCR as described in other examples herein. Data are averages from three experiments in which b.END cells were treated with the antisense oligonucleotides of the present invention. If present, "N.D." indicates "no data".

TABLE 4

Inhibition of mouse DGAT-1 mRNA levels by chimeric phosphorothioate oligonucleotides having 2'-MOE wings and a deoxy gap

| CMPD # | REGION | TARGET SEQ ID NO | TARGET SITE | SEQUENCE | % INHIB | SEQ ID NO |
|---|---|---|---|---|---|---|
| 191723 | 5'UTR | 7 | 1 | ctacttatttccattcatcc | 2 | 58 |
| 191724 | 5'UTR | 7 | 21 | tatcctaagtatgcctaatt | 0 | 59 |
| 191725 | 5'UTR | 7 | 31 | gcttgagccctatcctaagt | 0 | 60 |
| 191726 | 5'UTR | 7 | 61 | ctcgtcgcggcccaatcttc | 21 | 61 |
| 191727 | Start Codon | 7 | 81 | cccatggcttcggcccgcac | 48 | 62 |
| 191729 | Coding | 7 | 191 | cagccgcgtctcgcacctcg | 74 | 63 |
| 191730 | Coding | 7 | 232 | cggagccggcgcgtcacccc | 63 | 64 |
| 191731 | Coding | 7 | 281 | ccacgctggtccgcccgtct | 67 | 65 |
| 191732 | Coding | 7 | 301 | cagatcccagtagccgtcgc | 59 | 66 |
| 191733 | Coding | 7 | 321 | tcttgcagacgatggcacct | 49 | 67 |
| 191734 | Coding | 7 | 371 | tcaggataccacgataattg | 48 | 68 |
| 191735 | Coding | 7 | 391 | cagcatcaccacacaccaat | 52 | 69 |

TABLE 4-continued

Inhibition of mouse DGAT-1 mRNA levels by chimeric phosphorothioate oligonucleotides having 2'-MOE wings and a deoxy gap

| CMPD # | REGION | TARGET SEQ ID NO | TARGET SITE | SEQUENCE | % INHIB | SEQ ID NO |
|---|---|---|---|---|---|---|
| 191736 | Coding | 7 | 411 | aaccttgcattactcaggat | 62 | 70 |
| 191737 | Coding | 7 | 451 | atccaccaggatgccatact | 29 | 71 |
| 191738 | Coding | 7 | 471 | agagacaccacctggatagg | 42 | 72 |
| 191740 | Coding | 7 | 601 | cagcagccccatctgctctg | 63 | 73 |
| 191741 | Coding | 7 | 621 | gccaggttaaccacatgtag | 58 | 74 |
| 191742 | Coding | 7 | 661 | aaccagtaaggccacagctg | 16 | 75 |
| 191743 | Coding | 7 | 681 | cccactggagtgatagactc | 42 | 76 |
| 191744 | Coding | 7 | 711 | atggagtatgatgccagagc | 53 | 77 |
| 191745 | Coding | 7 | 771 | acccttcgctggcggcacca | 68 | 78 |
| 191746 | Coding | 7 | 841 | tggatagctcacagcttgct | 56 | 79 |
| 191747 | Coding | 7 | 861 | tctcggtaggtcaggttgtc | 32 | 80 |
| 191748 | Coding | 7 | 961 | ctcaagaactcgtcgtagca | 60 | 81 |
| 191749 | Coding | 7 | 1001 | gttggatcagccccacttga | 37 | 82 |
| 191750 | Coding | 7 | 1061 | gtgaatagtccatatccttg | 48 | 83 |
| 191751 | Coding | 7 | 1081 | taagagacgctcaatgatcc | 18 | 84 |
| 191752 | Coding | 7 | 1161 | tctgccacagcattgagaca | 50 | 85 |
| 191753 | Coding | 7 | 1201 | ccaatctctgtagaactcgc | 55 | 86 |
| 191754 | Coding | 7 | 1221 | gtgacagactcagcattcca | 56 | 87 |
| 191755 | Coding | 7 | 1271 | gtctgatgcaccacttgtgc | 72 | 88 |
| 191756 | Coding | 7 | 1301 | tgccatgtctgagcataggc | 70 | 89 |
| 191757 | Coding | 7 | 1331 | atactcctgtcctggccacc | 65 | 90 |
| 191759 | Coding | 7 | 1471 | attgccatagttcccttgga | 68 | 91 |
| 191760 | Coding | 7 | 1491 | agtgtcacccacacagctgc | 66 | 92 |
| 191761 | Coding | 7 | 1511 | ccaccggttgcccaatgatg | 71 | 93 |
| 191762 | Coding | 7 | 1531 | gtggacatacatgagcacag | 62 | 94 |
| 191763 | Coding | 7 | 1551 | tagttgagcacgtagtagtc | 40 | 95 |
| 191764 | Stop Codon | 7 | 1586 | ctttggcagtagctcatacc | 37 | 96 |
| 191765 | 3'UTR | 7 | 1621 | tccagaactccaggcccagg | 59 | 97 |

As shown in Table 2, SEQ ID Nos. 63, 64, 65, 66, 69, 70, 73, 74, 77, 78, 79, 81, 85, 86, 87, 88, 89, 90, 91, 92, 93, 94 and 97 demonstrated at least 50% inhibition of mouse DGAT-1 expression in this experiment and are therefore preferred. More preferred are SEQ ID Nos. 63, 88, 91, and 93. The target regions to which these preferred sequences are complementary are herein referred to as "preferred target segments" and are therefore preferred for targeting by compounds of the present invention. These preferred target segments of the mRNA are shown in Table 3 as the appropriate RNA sequence, where thymine (T) has been replaced with uracil (U) to reflect correct representation of an RNA sequence. The sequences represent the reverse complement of the preferred antisense compounds shown in Tables 1 and 2. "Target site" indicates the first (5'-most) nucleotide number on the particular target nucleic acid to which the oligonucleotide binds. Also shown in Table 3 is the species in which each of the preferred target segments was found.

EXAMPLE 5

Western Blot Analysis of DGAT-1 Levels

Western blot analysis (immunoblot analysis) is carried out using standard methods. Cells are harvested 16-20 h after oligonucleotide treatment, washed once with PBS, suspended in Laemmli buffer (100 μL/well), boiled for 5 minutes and loaded on a 16% SDS-PAGE gel. Gels are run for 1.5 hours at 150 V, and transferred to membrane for western blotting. Appropriate primary antibody directed to DGAT-1 is used, with a radiolabeled or fluorescently labeled secondary antibody directed against the primary antibody species. Bands are visualized using a PHOSPHORIMAGER® instrument (Molecular Dynamics, Sunnyvale Calif.).

EXAMPLE 6

Antisense Inhibition of Mouse DGAT-1 Expression: Dose Response in b.END Cells

In accordance with the present invention, six oligonucleotides targeted to mouse DGAT-1, CMPD#191729 (SEQ ID NO: 63), CMPD#191731 (SEQ ID NO: 65), CMPD#191755 (SEQ ID NO: 88), CMPD#191756 (SEQ ID NO: 89), CMPD#191759 (SEQ ID NO: 91), and CMPD#191761 (SEQ ID NO: 93), were further investigated in a dose response study.

In the dose-response experiment, with mRNA levels as the endpoint, b.END cells were treated with CMPD#191729, CMPD#191731, CMPD#191755, CMPD#191756, CMPD#191759, or CMPD#191761 at doses of 1, 5, 10, 25, 50, and 100 nM oligonucleotide. Data were obtained by real-time quantitative PCR as described in other examples herein and are averaged from three experiments and are normalized to untreated control cells. The data are shown in Table 5.

TABLE 5

Inhibition of mouse DGAT-1 mRNA levels by chimeric phosphorothioate oligonucleotides having 2'-MOE wings and a deoxy gap: dose response

| CMPD # | SEQ ID NO | Dose (nM) | | | | | |
|---|---|---|---|---|---|---|---|
| | | 1 | 5 | 10 | 25 | 50 | 100 |
| | | | | % Inhibition | | | |
| 191729 | 63 | 26 | 62 | 78 | 80 | 83 | 83 |
| 191731 | 65 | 27 | 58 | 57 | 58 | 82 | 85 |
| 191755 | 88 | 41 | 59 | 72 | 75 | 83 | 79 |
| 191756 | 89 | 13 | 39 | 59 | 65 | 81 | 75 |
| 191759 | 91 | 26 | 44 | 74 | 80 | 82 | 86 |
| 191761 | 93 | 23 | 63 | 71 | 80 | 85 | 87 |

These data presented in Table 5 indicate that the antisense compounds are capable of reducing DGAT-1 mRNA levels in a dose-dependent manner.

EXAMPLE 7

Effects of Antisense Inhibition of DGAT-1 (CMPD#191761) on Liver Fibrosis—In Vivo Studies Leptin is a hormone produced by fat that regulates appetite. Deficiencies in this hormone in both humans and non-human animals lead to obesity. db/db mice have a mutation in the leptin receptor gene which results in obesity, hyperglycemia and fatty liver, and so, these mice are good models of non-alcoholic steatohepatitis (NASH). In this example, oligomeric compounds of the present invention are tested in the db/db NASH model.

Six-week old male C57Bl/6J-Lepr db/db mice (Jackson Laboratory, Bar Harbor, Me.) are fed a control diet (chow. n=6) or a methionine choline deficient diet (MCD diet). The MCD diet mice were further separated into placebo groups (saline treatment) or treatment groups (DGAT-1 antisense compound treatment). The placebo and treatment groups were injected intraperitoneally with saline or antisense compound, accordingly, twice a week for either four weeks (n=8) or for eight weeks (n=7). For both the four week treatment and the eight week treatment there were placebo mice member and treatment mice members. The treatment group received 25 mg/kg of CMPD#191761 per each injection. At the end of the treatment period serum was drawn and the mice were sacrificed.

Expression of DGAT-1, TNF.alpha, TGF.beta, aSMA, collagen and TIMP-1 mRNA was evaluated using real time PCR of total RNA from whole liver tissues. Liver steatosis was evaluated by triglyceride content using Hematoxylin-Eosin (HE) and red-oil staining. Serum ALT and other serum parameters were also measured.

Figure 2:
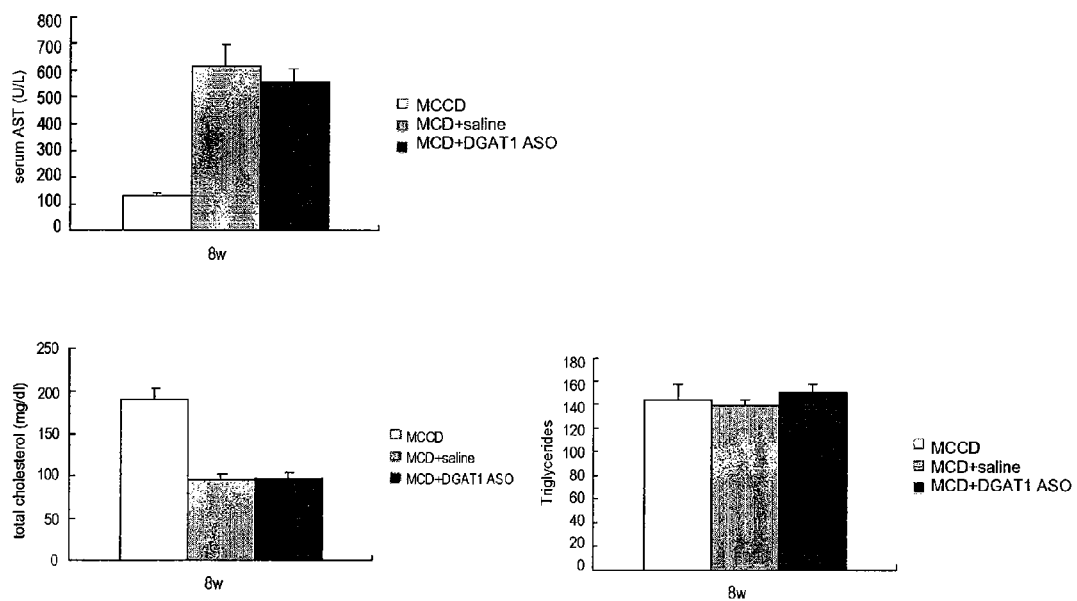
FIG. 2 is plasma biochemistry data for the control, placebo and DGAT-1 treatment groups.
Figure 3:
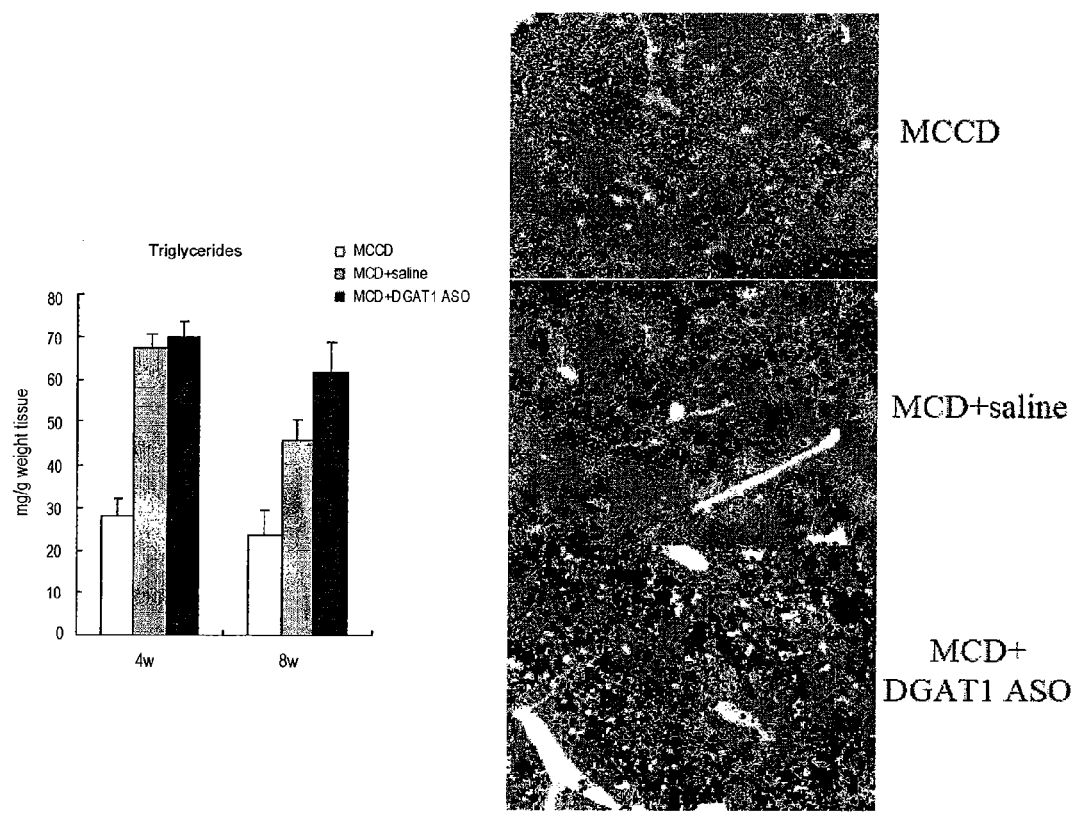
FIG. 3 illustrates that DGAT-1 treatment did not improve liver statosis, as indicated by liver triglyceride levels and Oil-Red stainind for the control, placebo and DGAT-1 treatment groups.

Hepatic stellate cells (HSC) and parenchymal cells were separated using standard techniques that are known to those ordinarily skilled in the art and DGAT-1 mRNA levels were determined. HSC expressed seven fold more DGAT-1 mRNA than did the hepatocytes. In the placebo group the DGAT-1 mRNA levels fell by about 70% at week 4, but returned to baseline by week 8. There was not a significant difference in the expression of DGAT-2 between the groups. Thus, the DGAT-1 antisense compound is specific for DGAT-1. (FIG. 1). The treatment group DGAT-1 mRNA fell by about 95% at week 4 and remained at that level at week 8. However, DGAT-1 antisense compound treatment did not protect the treatment group from hepatic steatosis. Liver triglyceride content and steatosis scores were similar for both the placebo group and the treatment group throughout the study (both groups being about 2-3 fold higher than the chow control group). Serum AST levels were similarly comparable for the placebo and treatment groups (618±80 and 557±49 v. 130±10 IU/L p<0.01). (FIGS. 2 and 3)

Figure 4:
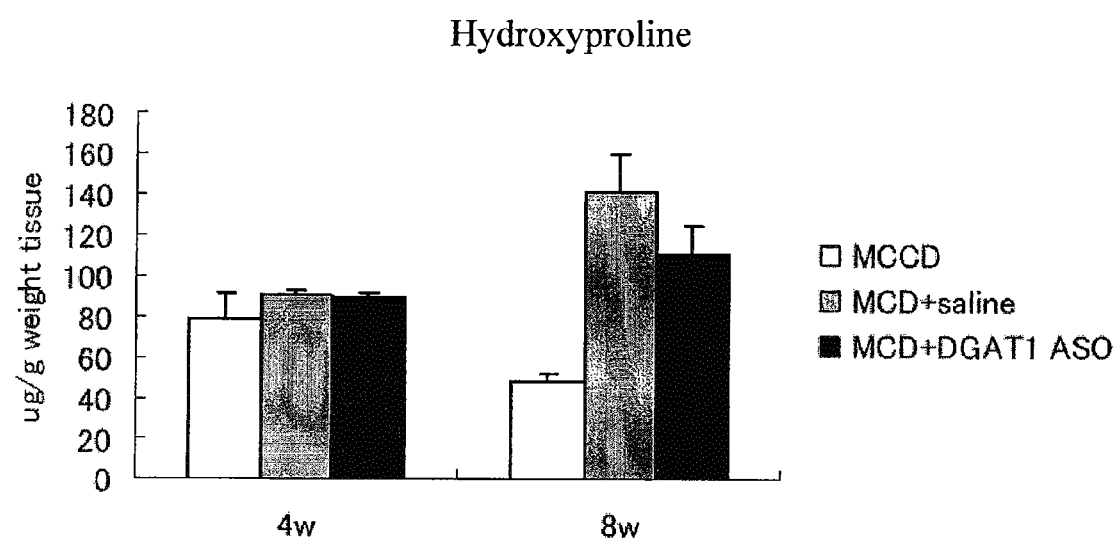
FIG. 4 is a graph showing changes in hydroxyproline at 4 weeks and 8 weeks for the three groups.
Figure 5:
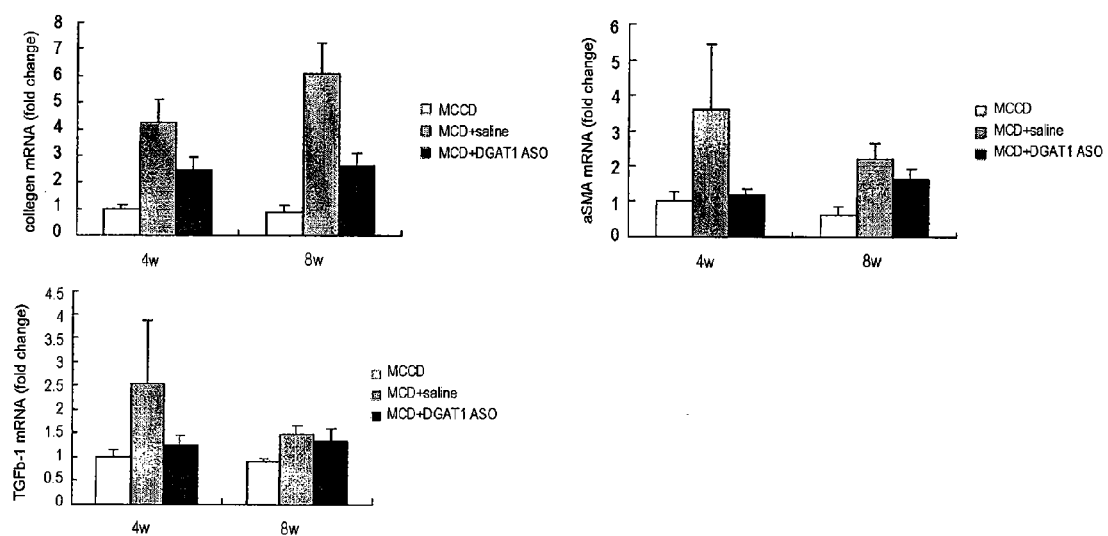
FIG. 5 illustrates the 4 week and 8 week differences in various factors of liver fibrosis for the control, placebo and DGAT-1 treatment groups.

Inhibition of DGAT-1 decreased MCD diet induced liver fibrosis. Compared to the livers of placebo group, the treatment group had less sirus-red staining and 20-30% lower levels of hepatic hydroxyproline (p<0.05 for both). (FIG. 4). Hepatic expression of TGF.beta., aSMA and collagen mRNA were decreased by 48%, 67% and 58%, respectively. (FIG. 5). Inhibiting DGAT-1 in the liver reduces both HSC activation and liver fibrosis in mouse models of NASH.

EXAMPLE 8

Effects of Antisense Inhibition of DGAT-2 (CMPD#217376) on Liver Fibrosis—In Vivo Studies DGAT-2 is expressed in hepatocytes and is associated with hepatic steatosis. Treatment with an antisense compound that inhibits DGAT-2 expression improves hepatic steatosis in obese mice (U.S. Patent Application No: US2005-0272680, incorporated herein by reference). Liver fat is a causative etiological factor for liver fibrosis.

Six-week old male C57Bl/6J-Lepr db/db mice (Jackson Laboratory, Bar Harbor, Me.) are fed one of a control diet (chow. n=6) or a methionine choline deficient diet (MCD diet). The MCD diet mice were further separated into placebo groups (saline treatment) or treatment groups (DGAT-2 antisense compound treatment). The placebo and treatment groups were injected intraperitoneally with saline or antisense compound, accordingly, twice a week for either four weeks (n=8) or for eight weeks (n=7). For both the four week treatment and the eight week treatment there were placebo mice member and treatment mice members. The treatment group received 25 mg/kg of CMPD#217376 (tccatttatt-agtctaggaa; SEQ ID NO: 99) per each injection.

CMPD#217376 is a chimeric oligonucleotides ("gapmers") 20 nucleotides in length and targeted to mouse DGAT-2 mRNA (Gen Bank Accession No: AK002443.1, Feb. 15, 2001, and SEQ ID NO: 100), composed of a central "gap" region consisting of ten 2'-deoxynucleotides, which is flanked on both sides (5' and 3' directions) by five-nucleotide "wings". The wings are composed of 2'-O-methoxyethyl (T-MOE) nucleotides. The internucleoside (backbone) linkages are phosphorothioate (P=S) throughout the oligonucleotide. All cytosine residues are 5-methyl cytosines. At the end of the treatment period serum was drawn and the mice were sacrificed.

Expression of DGAT-2, TNF.alpha, TGF.beta, aSMA, collagen and TIMP-1 mRNA was evaluated using real time PCR of total RNA from whole liver tissues. Cells were isolated using standard techniques that are known to those ordinarily skilled in the rat. Liver steatosis was evaluated by triglyceride content using Hematoxylin-Eosin (HE) and red-oil staining. Serum ALT and other serum parameters were also measured.

Figure 6:
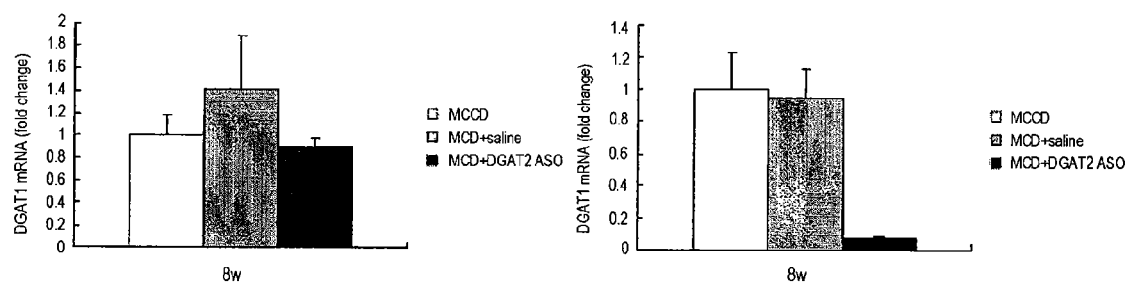
FIG. 6 is a series of graphs of DGAT-1 mRNA expression and DGAT-2 mRNA expression from liver tissue of mice either in the control groups (normal chow), the placebo group (MCD diet and saline) or the treatment group (MCD diet and DGAT-2 ASO treatment). Results are 8 week.
Figure 7:
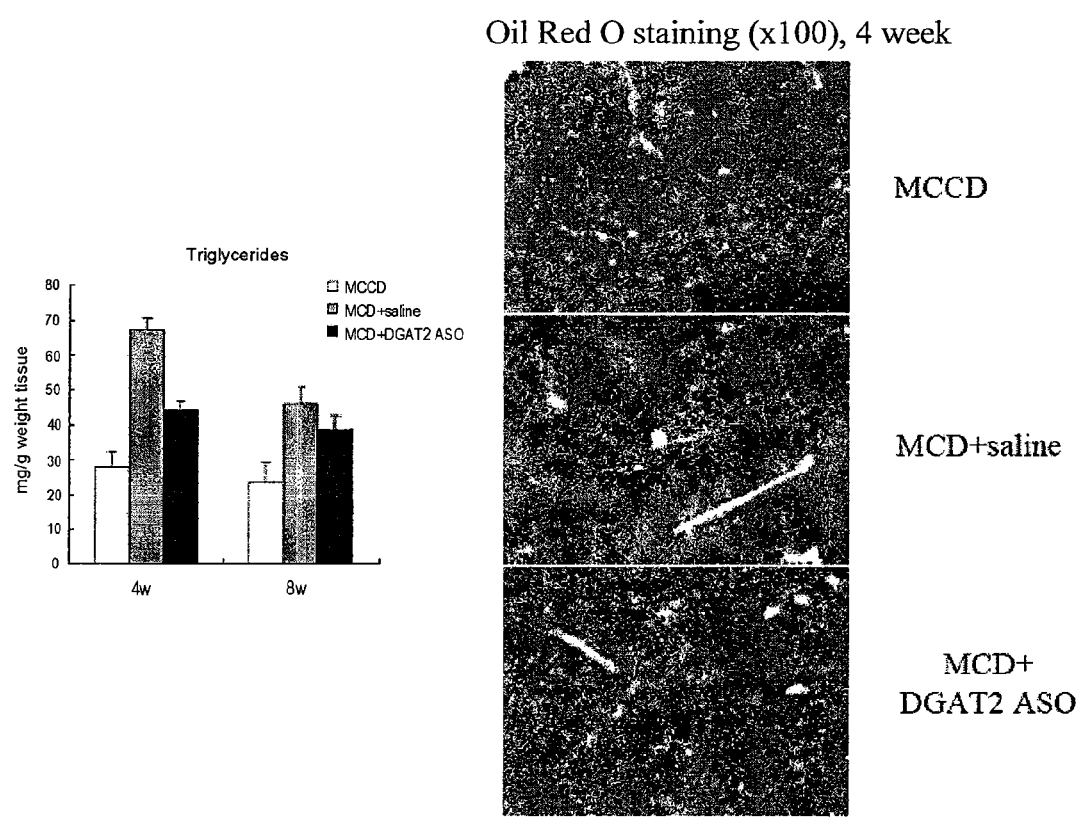
FIG. 7 illustrates that DGAT-2 treatment improved liver statosis, as indicated by liver triglyceride levels and Oil-Red stainind for the control, placebo and DGAT-2 treatment groups.
Figure 8:
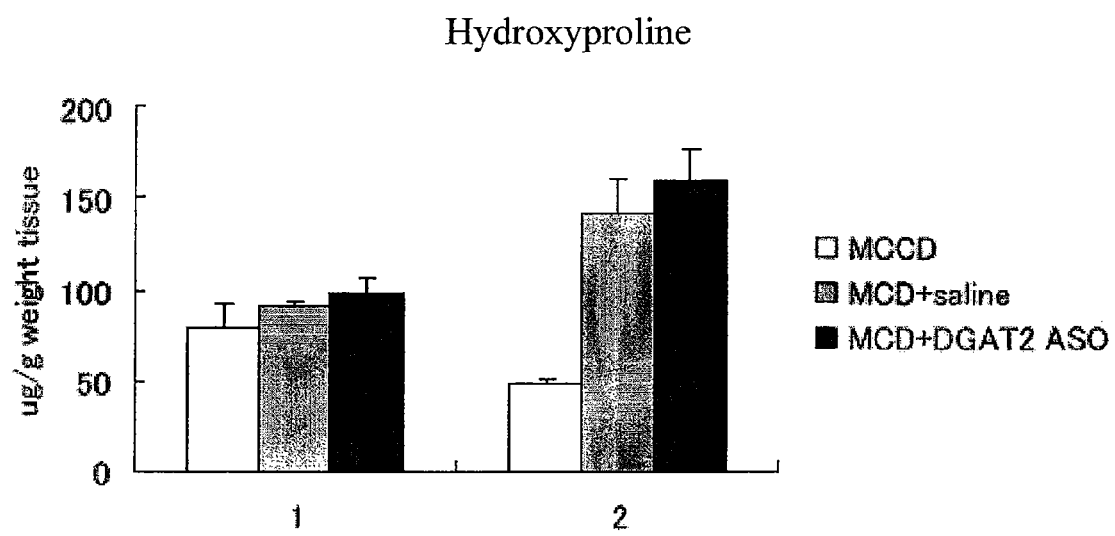
FIG. 8 is a graph showing changes in hydroxyproline at 4 weeks and 8 weeks for the three groups.

Hepatic stellate cells (HSC) and parenchymal cells were separated using standard techniques that are known to those ordinarily skilled in the art and DGAT-1 mRNA levels were determined. Hepatocytes expressed about 150 fold more DGAT-2 mRNA than did HSC. Hepatic expression of DGAT-2 mRNA was not changed by MCD feed compared to normal chow. But, there was a 90% greater reduction in DGAT-2 expression for the treatment group compared to the placebo group (8 weeks; p<0.001 v. controls). DGAT-2 antisense compound did not significantly change the expression of DGAT-1. (FIG. 6) Liver triglyceride content was increased about 2 fold for the control group over the placebo group. Similarly, serum ALT levels, and hepatic expression of TGF-.beta., a-SMA, TIMP-1 and collagen mRNA was increased 6-fold, 2-fold, 4-fold, 10-fold and 6-fold, respectively, in the control mice over the placebo mice (p<0.01 v. control). Hydroxyproline was 40% higher in the MCD diet group compared to the control group (8 weeks; p<0.05), and Sirius red staining was increased. (FIGS. 7 and 8)

Figure 9:
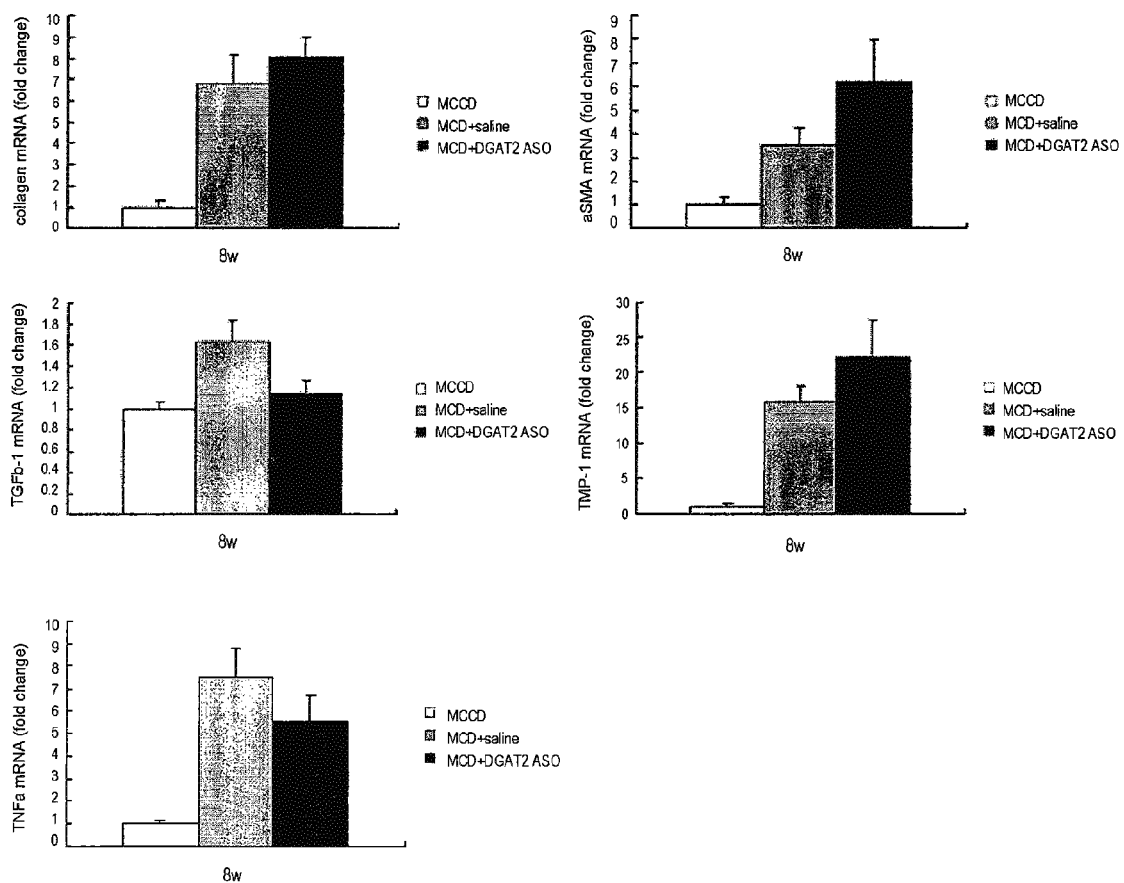
FIG. 9 is a series of graphs that illustrates the effect of DGAT-2 treatment on the expression of HSC activating mRNA. These results are at 8 weeks.

The treatment group had a reduced hepatic steatosis score compared to the placebo group (treatment group score 1 v. placebo group score 4), and hepatic triglyceride content was reduced by about 35% for the treatment group. Hepatic mRNA levels for TNF.alpha. and TGF.beta. were reduced in the treatment group, but there was an increase in the levels of serum ALT, hepatic a-SMA mRNA and TIMP-1 by 3 fold, 2 fold and 2 fold, respectively. (FIG. 9) There were no significant differences between the placebo group and the treatment group for the hepatic expression of collagen and fibronectin mRNA. DGAT-2 is an effective treatment for liver statosis; however, in this mouse model following 8 weeks of treatment there is not a significant improvement in liver fibrosis.

EXAMPLE 9

Antisense Inhibition of Rat DGAT-1 Expression by Chimeric Phosphorothioate Oligonucleotides Having 2'-MOE Wings and a Deoxy Gap A series of antisense compounds was designed to target different regions of the rat DGAT-1 RNA, using published sequence information (GenBank accession number AF296131.1, incorporated herein as SEQ ID NO: 101). The compounds are shown in Table 6. "Target site" indicates the first (5'-most) nucleotide number on the particular target sequence to which the compound binds. All compounds in Table 6 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytosine residues are 5-methyl cytosine.

The compounds were analyzed for their effect on rat DGAT-1 mRNA levels by quantitative real-time PCR as described in other examples herein. Probes and primers to rat DGAT-1 were designed to hybridize to a rat DGAT-1 sequence, using published sequence information (GenBank accession number AF296131.1, incorporated herein as SEQ ID NO: 101). For rat DGAT-1 the PCR primers were: forward primer: CAGACCAGCGTGGGCG (SEQ ID NO: 102); reverse primer: GAACAAAGAGTCTTGCAGACGATG (SEQ ID NO: 103) and the PCR probe was: FAM-CGGC-CACTGGGAGCTGAGGTG-TAMRA (SEQ ID NO: 104) where FAM is the fluorescent reporter dye and TAMRA is the quencher dye. Rat target gene quantities were normalized by quantifying total RNA using RiboGreen™ RNA quantification reagent.

Data are averages from three experiments in which rat primary hepatocytes were treated with 50 nM of the antisense oligonucleotides of the present invention. Data, shown in Table 6, are presented as percent inhibition normalized to untreated control samples.

TABLE 6

Inhibition of rat DGAT-1 mRNA levels by chimeric phosphorothioate oligonucleotides having 2'-MOE wings and a deoxy gap

| CMPD # | REGION | TARGET SEQ ID NO | TARGET SITE | SEQUENCE | % INHIB | SEQ ID NO |
|---|---|---|---|---|---|---|
| 191726 | 5'UTR | 7 | 1 | ctcgtcgcggcccaatcttc | 0 | 61 |
| 191733 | Coding | 7 | 261 | tcttgcagacgatggcacct | 68 | 67 |
| 327788 | Start Codon | 101 | 24 | TCGCCCATGGCTTCGGCCCG | 0 | 105 |
| 327789 | Coding | 101 | 44 | AGCTTCCCGCGCCTCCGCGG | 0 | 106 |
| 327790 | Coding | 101 | 61 | GGTCCTGCGACGCCGAGAGC | 0 | 107 |
| 327791 | Coding | 101 | 82 | CTGGACGGAAACCCGCGAGC | 0 | 108 |
| 327792 | Coding | 101 | 103 | TACCTTGGGCCCACTACCTC | 0 | 109 |

TABLE 6-continued

Inhibition of rat DGAT-1 mRNA levels by chimeric phosphorothioate oligonucleotides having 2'-MOE wings and a deoxy gap

| CMPD # | REGION | TARGET SEQ ID NO | TARGET SITE | SEQUENCE | % INHIB | SEQ ID NO |
|---|---|---|---|---|---|---|
| 327793 | Coding | 101 | 121 | TCGCACCTCGTCCTCTTCTA | 0 | 110 |
| 327794 | Coding | 101 | 170 | GAGCCGGCGCGTCACCCCCG | 0 | 111 |
| 327795 | Coding | 101 | 191 | TATGGGCTGGAGCCGGAGCC | 0 | 112 |
| 327796 | Coding | 101 | 196 | CCGGGTATGGGCTGGAGCCG | 0 | 113 |
| 327797 | Coding | 101 | 225 | TCGCCCACGCTGGTCTGCCG | 63 | 114 |
| 327798 | Coding | 101 | 248 | GGCACCTCAGCTCCCAGTGG | 64 | 115 |
| 327799 | Coding | 101 | 282 | CTGTCTGAGCTGAACAAAGA | 0 | 116 |
| 327800 | Coding | 101 | 309 | AGGATACCACGGTAATTGCT | 0 | 117 |
| 327801 | Coding | 101 | 318 | CACCAATTCAGGATACCACG | 0 | 118 |
| 327802 | Coding | 101 | 345 | GCATTACTCAGGATCAGCAT | 0 | 119 |
| 327803 | Coding | 101 | 359 | CTAAAGATAACCTTGCATTA | 0 | 120 |
| 327804 | Coding | 101 | 374 | ACTTGATAAGATTCTCTAAA | 0 | 121 |
| 327805 | Coding | 101 | 389 | CCACCAGGATGCCATACTTG | 0 | 122 |
| 327806 | Coding | 101 | 393 | GGATCCACCAGGATGCCATA | 0 | 123 |
| 327807 | Coding | 101 | 415 | AAACAGAGACACCACCTGGA | 0 | 124 |
| 327808 | Coding | 101 | 463 | GGATGCAATGATCAAGCATG | 0 | 125 |
| 327809 | Coding | 101 | 477 | ACAATAAAGATATTGGATGC | 0 | 126 |
| 327810 | Coding | 101 | 499 | CTTCTCAATCTGAAATGTAG | 0 | 127 |
| 327811 | Coding | 101 | 504 | AGGCGCTTCTCAATCTGAAA | 0 | 128 |
| 327812 | Coding | 101 | 527 | GCTCTGTCAGGGCACCCACT | 0 | 129 |
| 327813 | Coding | 101 | 537 | AGCCCCATCTGCTCTGTCAG | 20 | 130 |
| 327814 | Coding | 101 | 552 | ACCACATGTAGCAGCAGCCC | 17 | 131 |
| 327815 | Coding | 101 | 579 | GGGAAGCAGATAATTGTGGC | 0 | 132 |
| 327816 | Coding | 101 | 594 | AAGGCCACAGCTGCTGGGAA | 0 | 133 |
| 327817 | Coding | 101 | 607 | AGACTCAACCAGTAAGGCCA | 25 | 134 |
| 327818 | Coding | 101 | 616 | TGGAGTGATAGACTCAACCA | 2 | 135 |
| 327819 | Coding | 101 | 649 | GGAGTATGATGCCAGAGCAA | 0 | 136 |
| 327820 | Coding | 101 | 661 | GAGGAAGATGATGGAGTATG | 0 | 137 |
| 327821 | Coding | 101 | 679 | CCGGTAGGAAGAAAGCTTGA | 0 | 138 |
| 327822 | Coding | 101 | 709 | CCTTCGCTGGCGGCACCACA | 29 | 139 |
| 327823 | Coding | 101 | 726 | ACAGCTTTGGCCTTGACCCT | 0 | 140 |
| 327824 | Coding | 101 | 744 | ACCTTCTTCCCTGCAGACAC | 0 | 141 |
| 327825 | Coding | 101 | 758 | CAGCAGCCCCACTGACCTTC | 6 | 142 |
| 327826 | Coding | 101 | 779 | GATAGCTTACAGTGTTCTGG | 0 | 143 |
| 327827 | Coding | 101 | 797 | GGTAGGTCAGGTTGTCCGGA | 0 | 144 |
| 327828 | Coding | 101 | 806 | AGAGATCTCGGTAGGTCAGG | 0 | 145 |

TABLE 6-continued

Inhibition of rat DGAT-1 mRNA levels by chimeric phosphorothioate oligonucleotides having 2'-MOE wings and a deoxy gap

| CMPD # | REGION | TARGET SEQ ID NO | TARGET SITE | SEQUENCE | % INHIB | SEQ ID NO |
|---|---|---|---|---|---|---|
| 327829 | Coding | 101 | 819 | AAGATGAAGTAATAGAGATC | 0 | 146 |
| 327830 | Coding | 101 | 833 | ACAAAGTAGGAGCAAAGATG | 0 | 147 |
| 327831 | Coding | 101 | 849 | AAGTTGAGTTCATAACACAA | 0 | 148 |
| 327832 | Coding | 101 | 912 | AAAAAGAGCATCTCAAGAAC | 0 | 149 |
| 327833 | Coding | 101 | 934 | CAGCCCCACTTGAAGCTGGG | 0 | 150 |
| 327834 | Coding | 101 | 949 | CATCCACTGCTGGATCAGCC | 0 | 151 |
| 327835 | Coding | 101 | 970 | GGAGTTCTGGATAGTAGGGA | 0 | 152 |
| 327836 | Coding | 101 | 981 | AAGGGCTTCATGGAGTTCTG | 0 | 153 |
| 327837 | Coding | 101 | 991 | CATGTCCTTGAAGGGCTTCA | 0 | 154 |
| 327838 | Coding | 101 | 1030 | CGCCAGCTTTAAGAGACGCT | 0 | 155 |
| 327839 | Coding | 101 | 1103 | GCTCTGCCACAGCATTGAGA | 0 | 156 |
| 327840 | Coding | 101 | 1131 | TAGAACTCGCGGTCTCCAAA | 0 | 157 |
| 327841 | Coding | 101 | 1162 | GGTGACAGACTCAGCATTCC | 0 | 158 |
| 327842 | Coding | 101 | 1186 | GATATTCCAGTTCTGCCAAA | 0 | 159 |
| 327843 | Coding | 101 | 1212 | TGTCTGATGCACCACTTGTG | 0 | 160 |
| 327844 | Coding | 101 | 1271 | AGACCCCAGTCCTGGCCATC | 22 | 161 |
| 327845 | Coding | 101 | 1299 | TACTCATGAAAGAAAGCTGA | 0 | 162 |
| 327846 | Coding | 101 | 1351 | CATTGCTGTGAATGCCCAAA | 0 | 163 |
| 327847 | Coding | 101 | 1380 | ACAATCCAGGCCAGTGGGAC | 0 | 164 |
| 327848 | Coding | 101 | 1414 | TGCATTGCCATAGTTCCCTT | 0 | 165 |
| 327849 | Coding | 101 | 1442 | GCCCAATGATGAGTGTCACC | 0 | 166 |
| 327850 | Coding | 101 | 1477 | GTAGTCGTGGACATACATGA | 0 | 167 |
| 327851 | Stop Codon | 101 | 1524 | TTGGCAGTAGCTCATGCCCC | 0 | 168 |
| 327852 | Stop Codon | 101 | 1531 | CTGGCCTTTGGCAGTAGCTC | 12 | 169 |
| 327853 | 3' UTR | 101 | 1562 | CCTCCAGAACTCCAGGCCCA | 55 | 170 |
| 327854 | 3' UTR | 101 | 1637 | ATCCCCAAGAGCAGGAGTAG | 0 | 171 |
| 327855 | 3' UTR | 101 | 1670 | CCCAGCACTGGCTCAACCAG | 0 | 172 |
| 327856 | 3' UTR | 101 | 1702 | TTGATATCCTAAGCCCCTGG | 0 | 173 |
| 327857 | 3' UTR | 101 | 1727 | TTTTTTTTTTTAGATAGCT | 0 | 174 |

As shown in Table 6, SEQ ID NOs 67, 114, 115, 130, 131, 134, 139, 161, 169 and 170 demonstrated at least 10% inhibition of rat DGAT-1 in this assay. SEQ ID NOs 61 and 67 are cross-species antisense oligonucleotides that target both mouse and rat DGAT-1.

EXAMPLE 30

Antisense Inhibition of Rat DGAT-1 by Chimeric Phosphorothioate Oligonucleotides Having 2'-MOE Wings and a Deoxy Gap: Dose Response In a further embodiment, six oligonucleotides were selected for further investigation in a dose response experiment in rat primary hepatocytes. Rat primary hepatocytes were treated with 1, 5, 10, 25, 50 and 100 nM of CMPD#191733 (SEQ ID NO: 67), CMPD#327798 (SEQ ID NO: 115), CMPD# 327814 (SEQ ID NO: 131), CMPD#327817 (SEQ ID NO: 134), CMPD#327822 (SEQ ID NO: 139), CMPD#327844 (SEQ ID NO: 161) and CMPD#327853 (SEQ ID NO: 170). Untreated cells served as a control. Target mRNA levels were measured by real-time PCR as described in other examples herein. Data, presented in Table 7, are the average of three experiments and are normalized to untreated control samples.

TABLE 7

Inhibition of rat DGAT-1 by chimeric phosphorothioate oligonucleotides: dose response

| CMPD # | SEQ ID NO | Dose of oligonucleotide | | | | | |
|---|---|---|---|---|---|---|---|
| | | 5 | 10 | 25 | 50 | 100 | 200 |
| | | % inhibition | | | | | |
| 191733 | 67 | 20 | 53 | 77 | 91 | 97 | 99 |
| 327798 | 115 | 0 | 13 | 68 | 88 | 96 | 98 |
| 327814 | 131 | 0 | 5 | 37 | 72 | 80 | 89 |
| 327817 | 134 | 0 | 0 | 0 | 57 | 76 | 87 |
| 327822 | 139 | 0 | 32 | 52 | 73 | 88 | 95 |
| 327844 | 161 | 0 | 0 | 17 | 66 | 71 | 87 |
| 327853 | 170 | 0 | 0 | 48 | 70 | 80 | 92 |

As demonstrated in Table 7, all 7 antisense oligonucleotides tested were able to inhibit the expression of DGAT-1 in a dose-dependent manner.

All documents referenced in this specification are incorporated by reference.

What is claimed is:

1. A method for preventing liver fibrosis comprising administering a modified oligonucleotide that decreases DGAT-1 expression.

2. The method of claim 1 wherein the modified oligonucleotide is a specific inhibitor of DGAT 1 expression.

3. The method of claim 2 wherein the modified oligonucleotide is an antisense compound targeted to a nucleic acid that is substantially similar to SEQ ID NO: 4 and that expresses DGAT-1.

4. The method of claim 3 wherein the modified oligonucleotide of DGAT-1 is a chimeric antisense compound comprising a consecutive nucleoside length of 12 to 50 nucleosides, further comprising one or more of a nucleobase modification, an internucleoside linkage modification, a high-affinity sugar modification or a combination thereof, and further comprising no more than three mismatches to the target nucleic acid sequence (SEQ ID NO: 4) that encodes DGAT-1.

5. The method of claim 4 wherein the nucleoside length is 14 to 35 nucleosides.

6. The method of claim 4 wherein the nucleoside length is 17 to 24 nucleosides.

7. The method of claim 4 wherein the chimeric antisense compound is 20 consecutive nucleosides in length.

8. The method of claim 4 wherein the internucleoside linkage modification is at least one phosphorothioate linkage.

9. The method of claim 8 wherein every internucleoside linkage is a phosphorothioate linkage.

10. The method of claim 4 wherein the high-affinity sugar modification is selected from the group consisting of a 2'-O-(2-methoxyethyl), a 2'-O-methyl, a locked nucleic acid or an ethylene-bridged nucleic acid.

11. The method of claim 10 wherein the high affinity modified sugar is a 2'-O-methoxyethyl sugar moiety.

12. The method of claim 4 wherein the nucleobase modification is a 5-methyl cytosine.

13. The method of claim 4 wherein the antisense compound comprises no mismatches to the target DGAT-1 encoding nucleic acid sequence.

14. The method of claim 4 wherein the antisense compound is 20 consecutive nucleosides in length, comprises five consecutive 2'-O-(2-methoxyethyl) sugar modifications at the 5' end of the compound, followed by ten consecutive 2'deoxy sugars which are followed by five consecutive 2'-O-(2-methoxyethyl) sugar modifications at the 3' end of the compound, also comprising a phosphorothioate linkage modification at every internucleoside linkage and a 5-methyl cytosine modification at every cytosine residue in the compound, and comprising no more than 3 mismatches to the target DGAT-1 encoding nucleic acid sequence.

15. The method of claim 4 wherein the antisense compound is 20 consecutive nucleosides in length, comprises five consecutive 2'-O-(2-methoxyethyl) sugar modifications at the 5' end of the compound, followed by ten consecutive 2'deoxy sugars which are followed by five consecutive 2'-O-(2-methoxyethyl) sugar modifications at the 3' end of the compound, also comprising a phosphorothioate linkage modification at every internucleoside linkage and a 5-methyl cytosine modification at every cytosine residue in the compound, and comprising no mismatches to the target DGAT-1 encoding nucleic acid sequence.

16. The method of claim 1 wherein administration of the modified oligonucleotide reduces collagen mRNA expression.

17. The method of claim 1 wherein administration of the modified oligonucleotide reduces of one or more of a-SMA mRNA, or a TGF-beta. mRNA.

18. The method of claim 1 wherein administration of the modified oligonucleotide reduces hydroxyproline levels.

19. The method of claim 1 wherein the administration of the modified oligonucleotide increases retinol esterification.

20. The method of claim 1 wherein the administration of the modified oligonucleotide reduces hepatic stellate cells activation.

21. A method for preventing liver fibrosis in an animal in need of such a treatment comprising contacting the animal with a modified oligonucleotide that decreases DGAT-1 expression.

22. The method of claim 21 wherein the animal has a condition that causes liver fibrosis, the condition selected from the group consisting of NASH and metabolic syndrome.

23. A method of preventing excessive collagen deposition in the liver of an animal in need of such a treatment comprising the step of contacting the animal with a modified oligonucleotide that decreases DGAT-1 expression.

24. The method of claim 23 wherein the animal has a condition that causes liver fibrosis, the condition selected from the group consisting of NASH and metabolic syndrome.

* * * * *

SEQUENCE LISTING

```
<160> NUMBER OF SEQ ID NOS: 174

<210> SEQ ID NO 1
<211> LENGTH: 384
<212> TYPE: DNA
<213> ORGANISM: Homo sapiens

<400> SEQUENCE: 1
tttccccgct ctccccgcat ccggaagcgc tttctgctgc gacggatcct tgagatgctg      60
ttcttcagcc agctccaggt ggggctgatc cagcagtgga tggtccccac catccagaac     120
tccatgaagc ccttcaaggt gagtggctca ggtgctcttg cagctggggt ggctggggag     180
tgaccaggag catggctagc tgaacggctt gtttctgcag gacatggact actcacgcat     240
catcgagcgc ctcctgaagc tggcggtccc caatcacctc atctggctca tcttcttcta     300
ctggctcttc cactcctgcc tgaatgccgt ggctgagctc atgcagtttg gagaccggga     360
gttctaccgg gactggtgga actc                                            384

<210> SEQ ID NO 2
<211> LENGTH: 494
<212> TYPE: DNA
<213> ORGANISM: Homo sapiens

<400> SEQUENCE: 2
gagccatcag tggatggtcc ccaccatcca gaactccatg aagcccttca aggacatgga      60
ctactcacgc atcatcgagt gcctcctgaa gctggcggtc cccaatcacc tcatctggct     120
catcttcttc tactggctct ccactcctg cctgaatgcc gtggctgagc tcatgcagtt     180
tggagaccgg gagttctacc gggactggtg gaactccgag tctgtcacct acttctggca     240
gaactggaac atccctgtgc acaagtggtg catcaggtag gtgggtgtg tgtgtgtgtg     300 atgtggaaca tggctgtgaa cctgaaccgc tttccatgcc cctcctctg cagacacttc     360 tacaagccca tgcttgacg gggcagcagc aagtggatgg ccaggacagg ggtgttcctg     420
gcctcggcct tcttccacga gtacctggtg agcgtccctc tgcgaatgtt ccgcctctgg     480
```
gcgttcacgg gcat 494

<210> SEQ ID NO 3
<211> LENGTH: 21001
<212> TYPE: DNA
<213> ORGANISM: Homo sapiens
<220> FEATURE:
<221> NAME/KEY: misc_feature
<222> LOCATION: (1)...(21001)
<223> OTHER INFORMATION: n = A,T,C or G

<400> SEQUENCE: 3

```
tctctactaa aaatacaaaa attagctggg catggtggtg cgtgcctgta gtgccagcta      60
ctcaggaggc tgaggcagga gaatcacttg aagtcaggag gcgggtttcg gtgagctaaa     120
attgcgccac tgcactccag cctggcgaca gagcgagact ccgtctcaaa aaacaaaaaa     180
agatctgcag aatgggcagc ctgtgtccat gccaccctca ctccctgcca ccctcaaggg     240
tgcccaggtg agatgggta ggggacagta tggacggtgg catcctctgg agagatgggg     300
ttccaaggct gtctgtgaag gtaaaggatg gcagcaaggg ggcagggctg aggcagcaga     360
ggtcacagga gggtcaaggt cacctgcagc ctgaggtcca ctaggaagag aggaggacac     420
caggagggtg ggtctccaag gcctggggag gcaaggtctg cagggaagag agcccagtta     480
aggcaggaag tggggacat cctgggtatc tgttgagcag gtactgggct cctgggggag     540
atttaggcaa gaggatgggg tagaggggtg tccccaggcc tggccccagt taggaggata     600
tcagggtggg agccctggga gaactctggg gaccagctgg gcagccctgg aatgaggcgc     660
caggcagcgg gcagaccaca cacaggtgca cagggagggg ctgaggtcag agtggcttct     720
ccaaggctgg ccatggccag aggcctgtcc ctgctttctg tnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn ncccgcatgt gccccgccgc cttgtacata ttcccacccg     900
gaataggccg ggattttac tcgggccgtg cccttcttcc gccccatttt ggggccaggc     960
cggccggaca gacggacgga cggacagacc tccttcctaa gcacaatagc accagctccc    1020
cggagcaccg cacctccaca aggagaataa atgccactct tgatagaatt tggagtgtcg    1080
ggctgatgtg tcctgggctg ggcccacgct gttgggtggc tgggagggtc ttcccagtct    1140
ggcagtacct cagaggctgg tgctgcaagg gtcagcctga ggccttttcac aagacggccc    1200
tcttcttcca ctggggaggg caggcttggc aggcccaacc acaggagcat caggtctgaa    1260
ggcaaagtag ttggcatttc ccctgggta ggtggatctg ctccacacca ggaacaggag    1320
cactaagggg ttccagtcta aagtcaggcc aagcccacgg ttggaccaga gtgggcaggg    1380
taggtatagt aggagctgct gttccccagc ctgggtgcct tcgctcttct ctccctgaag    1440
gagctttatg ctgtgatgga aggcctgata gccacctcaa gccctctgag atgctgttgc    1500
aggaaatggg gacagtggag agttcgaggt ctggcccttt tcctgtggcc tgctgcccac    1560
attctgaccc ccaggcttcc cagatatgct cccccagtgt ctgcggatgc ctccatggat    1620
agctgggttg gaccggttcc agggaggagg tgcccagggg gcagagaggc ttctgcaacc    1680
atcgcccaag ggctctagac agaatgagta gtggaggaga taagggacag ggacccttttg   1740
cccagcaatg tcccctggta accaggtagg caggcatgag ccgagaggcc caaagtcttc    1800
gggcacatac attcaaacca ggtcagtcct agatccaggg ccagcaaagc tgcccacacc    1860
ctagcaggga caggggacag acctgcccag actccactag gtggagagc agggaacca    1920
ggtctgcagc atgtcatggc ctgtgtgcct ggcacttgga ggagctgtgg tgcaggtggg    1980
```

```
tgctctcttt gggagagcac taccagcaat gacaatggca gacagcaatg gccaggagga   2040
aggctcctag cctcactcct tccaaaggac tccaacagcg actggctgtt tctacttctc   2100
caggattctg atgcgtagag tgggtggaag gatggaggtg gcctccctga ggcctgggat   2160
gagctcgacc ccccagttcc tcccagccac agacactagt ttccctctga atgagcagca   2220
caggccatag accaccactg gctgtgaact ctcctgggac ccttgcttct cacaggcctt   2280
cttggcccac ccatggcccc taggccctgg gatcagcctg aggccccaac ccacttccag   2340
ccctttattc cactagccct ggaaggcaac tcgcttcggg cttgggcccc tcatttgtt    2400 gctgccccca gcagggtgat ctgcatcatg cttcctcga tgacccagcc atacacaccc    2460
ttgtccccaa ccaacctcac ctaccctgac cattcccctc accctatatc cagggtata    2520 gggcctgtct gggcagggct tcacccacct ctggagctgc tgccccgcca cgcccccacc   2580
cccggtggca aagcccttcc ttaatggccc gcccacagcc agtgctttcc ccattggctc   2640
caagcctggc tctgctcacc aggcccgacc catcctccct ggtggtccag tccaccctcc   2700
cattgtcttt ctcctgtggc cacttgccgg cttttgagttg ggacgcgacc acaggttgag  2760
tcgttgatct cctctgccta gcatgaggtg ctccgtggcc aggtccagac ctctctgagc   2820
ttgctgtcag tccatactca gacaggtctg ggcctacctg gccacagagt gtgtctgcca   2880
gcgactgcat tcaacaaatg aatattctga gagactgggt aggagatggg gctggtcctg   2940
accgaccaag gcccatgtgt gaggggctct tgggtccagt gagggcggcc ccactcggca   3000
ggctacacaa agggcatctg ccaggtagct ccagcctgcc tgatacctgg ttggcagcaa   3060
cccacagcgg cctgtggtga caagaatatg tcaccagggg ggcaaccaag ggggcagccc   3120
tgctggccac tgttggtgga ggtggtggaa gaggacggag ctcagaggcg aggctgtgac   3180
cagcccacgg gagaggaccc cacctcagga ggagcacctg tttgcttcca gagaagtgct   3240
gcttgcccct gctcaccccca gaggaatgaa ggtgtttcta gagtcagagt cctcagtgaa   3300
ccctggcatc ctgagatcca ggatgttctc actccatgcc ctgtgcaata tgcacaccaa   3360
gccaaggtgg gccgcaactg tggctgttac agttgattag ttgcttcatt taacatacaa   3420
gatgtctggg gcagtggctc atacctgtaa tcccagcacc ttcagaggcc gaggtgggag   3480
gattgcgtga ggccaggagt tcgagaccag cctgggcaga atagcgagac ccccatcttt   3540
agaaaaaata caacaggcc aggcgcggtg gcttgcgcct ataatcccag cactttggga   3600
ggccgaggtg ggcggatcac gaggtcagga gatcgagacc agcctggcca atatggtgaa   3660
agcccgtctc tactaaaaac agaaaaatta gctgggcgtg gtggcacgcg cctgtagtcc   3720
tggctactcg ggaggctgag gcaggagaat cgcttgaacc caggaggtgg aggttgcagt   3780
gagacgagat cgcgctactg cactccagcc tggcgacaga gtgagactgt ctcaaaaaaa   3840 gaaaaagaa acaaaaaac aacagggcgg ttgcacaggc cgtgcaaatg cacagaagcc    3900
tcttgagtcc cggcgatcca gcgcccaga cttctgacat cctggagagg ctggcccacg    3960
ttggaaactg ggaggccctg agagttgagg gacgtggagc tccttgtgga gagagtgggt   4020
gggctgagaa gacaccacca aggggcctgc gccctcgccc tcgccctcgc cctcctctcg   4080
ccgggctctg caggcgggga ggtggagagc ctgggagtcg cgtgcaaggc aggcgtcccg   4140
gtgacgcagg gcctggtgca tttctccagc ttggtcttct gacctggccc ttgtctgacg   4200 tcccctaag gcgaagaaaa gcaggttcct gccggggtaa ccagagggct cgcggagcag    4260
aagcgcgcca gggacgttac tgtaagctgc gtgcgcagaa accaacgcgc tgggtggcgg   4320
gcgacgcgag ccgccgcgga caccggcccg gacagctgga ccgtggcgca ctaggcgctt   4380
```

```
cctaaatgat tgcccggagt gactcgccga gaccccgtgt gtacacaagt gggacgaggg   4440
gcgggcgcac agcggccagg aagtcggggc ccagccgcacc cctcagcgga ccatcccgct  4500
ccgtggggcc ggacaggacc ccgggaccac gcgggagcga tgcaaggtcc gttcccgctg   4560
cgcgcacttg cggcccgcag ccccggccct gggagctgcc acggctccca gggtgttctg   4620
cgccggtgcg gccgcggcga ctacgactcc caggtgctc tgcgccggcg cgcccgcggc    4680
gactacgact cccagggtgc cctgcgcccc gtcagcctct ccaggcccg cctcaggtcg    4740 gccgcggact acaaatggac gagagaggcg gccgtccatt agttagcggc tccggagcaa   4800
cgcagccgtt gtccttgagg ccgacggcc tgacgcgggc gggttgaacg cgctggtgag    4860
gcggtcaccc gggctacggc ggccggcagg gggcagtggc ggccgttgtc tagggcccgg   4920
aggtggggcc gcgcgcctcg ggcgctacga acccggcagg cccacgcttg gctgcggccg   4980
ggtgcgggct gaggccatgg gcgaccgcgg cagctcccgg cgccggagga cagggtcgcg   5040
gccctcgagc cacggcggcg gcgggcctgc ggcggcggaa gaggaggtgc gggacgccgc   5100
tgcgggcccc gacgtgggag ccgcggggga cgcgccagcc ccggccccca acaaggacgg   5160
agacgccggc gtgggcagcg gccactggga gctgaggtag cggagcgcct gacccctaa    5220 cctctgaccc aagggccccg cgactttccg gggttggccg aagcgcgagc tccgagtccg   5280
agaacatggg ccctgggcta agcggggatc ggtgtgccct atgggccctg tggggaaact   5340
gaggcttggg gagagtcacc tgacaaggtc actgggtagg ggctctggag ctggccttgg   5400
ccaggcagag gggagccggc aggtgtcccg catccagatc ctcttgggtc tgtgcatcct   5460
caggggctcc tgaggagctt ttcgagggc gggctggtgg gggcccggcc ctggacagtg    5520
tccccttata tggaaggagt cagataagat ctgggcagtt tgtggtgata ggttctttct   5580
tggtgctatg agcggtgcct tgcgggtagg aaaggctccc agaggagggc tggcctgcca   5640
gggagggggc cagaggagcc caggcctgtc cgaggacagg ggaatcagca gctgccccgg   5700
acaagggcga gtgttagagg cgttcttgtc cttgcagacc cttctgagag tggctgcgtg   5760
gcccattcat tgctccagtg gttaggctgg cctggagccc tgccgatgtt gccagagcca   5820
gcgtctgttg tagggacaga gagttgggtt ctgtgttggg acttccatcc tccaggtggg   5880
gagtggggta tgggggtggt ggacacacct gcaggcgtgt gccctgctca gctggatgac   5940
tgacagagag gggtggaggg agagaaccat ggccgatggg aaggacttgg ccagcctggg   6000
cattggcttc ctccaccaag ctggccttga gcaatcccct tgccaccctc catcccccct   6060
ttatggcctt taccctggcc caggggccct cagggctttg ttttagagag cagctgaggg   6120
cctagaggtt atcaaggcag aagtgggctg atttttggaca tgtagttggc aatgatttgc   6180
tctctcagtg agcaagaaca gagctttcct tcacggggca ccatggggag ggggttgggg   6240
gagggcaggc actgtcgtgg ccctcagggt gctcagttca tctgggagat aagataacct   6300
cagcaagagt caggcatgga gcaacatgga caaaggtcgg gcacgaggc cttgaagggg    6360 ccgtggggag gagggtggcc ctcctgagag gggtgcttgc ctgctgtggg cctggggtgc   6420
tggtgaggga ggctggccta ggcacctcct acctgaaaag gaggtgtggc tcctggagtt   6480
accctctctc caggaggcag ggggatggct acatgacctg tggaggacgt gggaattgag   6540
atttcttttt ttttctttc tttttttttg agactagttt tgctcttgtt gcccaggctg    6600
gagtaaaatg gcacattctt ggctcactgc aacctctgcc tcccaggttc aagtgattct   6660
cctgcctcag cctccagagt agctgggatt agaggcgccc accacacccg gctaattttg   6720 tattttagt aaagatgggg tttctccatg ttggtcaggc tggtctcgaa ctcctgaact    6780
```

```
caggtgatcc acctgccttg gcctcccaaa gtgctgggat tacaggtgtg agccaccgcg    6840
cccggccggg aattgagatt ttttttagtg tgagatgagg gtagtcccag ctttgggcca    6900
agccgccacc tgggggtagg caggggagag cagtcacctt cttgctttgc aaaccagcaa    6960
ggctttcctg tacttctgct ggtgtgggat gggtgcagag ctcgtgggag aggcctggtg    7020
agtccctgtc cctgccgtgg aggtcgggtc tccttgggaa gaggggcagt agatggagag    7080
gtgaggcctt catggggctg gaggctgaga ccaaaagtct atctgctcct gggtctccag    7140
gacttgcagg ctatgtgtgc ttgtccctca gacctaggga tgcagcaggg ctcggccact    7200
ggctgtggac actgggctct tctccctgct gtctgcgtca ggccttgctc tgcctgccct    7260
cctgggactt ggcctctagc gcaccccctt gtcagcctca cagcctcccc tccctccagc    7320
ttcctgctgc tcttggccca gcccagcctt cctctcccg cttcctcatt actccttgag    7380
ctcgggcctc ctcccctcac ggacacttcc tgctcaccta gggctgggct ctgggtgtga    7440
gctcctttct tccggccccg tggcaaggtg aggctgtgag gcaggcagga gagggcaccc    7500
ctttctgctc tgcttgtggc tcactcctgc caggctcttt gcacacaccc accagccctc    7560
tgctcacagg caccccagtt ggggccatcc ggtttctggc ttctcccagg gtgttttgtc    7620
cctgaggtgt cctttctaac tctccctttc tctctccagc agggtctgcg aggtgcaggg    7680
agcctgcccc aaccatcttg aacccaggcc cagcccagag gccagagtgg aggaggcggc    7740
agtgagcaga gctggactct gccccctcct cattgtgctt ggccctggag ctgcactgtg    7800
tgggccccaa gtgtgggact cactgggacc tgtgcctttg gcacacttt gaacctggag    7860 acagggtggc gggtgggcat gtgccaaggt ctcagtgttg ccgtgagact gagaggatcc    7920
tgctggctgg gtgggcctgg gggctgcagg agggagggca ggctgctccg agtcttcttg    7980
gactagggag tgggtgtagg gacagctgga aggtgcagag gcttgggcag atcctccagt    8040
cagtgagagg gtgataaagg tgctttaggc acagggcag atcccacctc cccatgccgt     8100
tccatgcagc ctgccctgta gcccacatgc tgctggccgc actgactgct ggagctctg    8160 tgggcactgg tggactgggg cttcctcctc atggggcct gtgaggggta ggggtagcgc    8220
agtgggggtg ctgcctctgg gtggggctgg tcaggcctgt gaagggcctg aggtgaggct    8280
gtggctgggt tgaggaaggc cttggaagcc tgtcaagggg cccctgagaa agcttgtgta    8340
ggattgtctg cagtgagctt tgggaagcac cacccttcc cgactcctgt tttcatcttg    8400
gagatgggca tggataaagc cagcatggtg tccttggtgg ctcaaagggg gcagggtca    8460 tactgctgtg aaacagctgt ggttggtagg tcgtggtaca agaaagccaa ccctgaggct    8520
tgggattgtt ctgctgaaaa caaatgggct cgaacttggg gaagagggg cagtggagag    8580 gcccccagac agacagccca gagaggctgc tgggcagttg ggcctcgtgc ccctgctccc    8640
gtcacggtgc tggggctctg gcggtgtcta cacccagcct cctggttgtg ggcaggcagt    8700
gagtggagta ggctggggag atgagccaag ggcggtggtc agttgggaag acagctgcca    8760
acttggggag gagggaggct ctggtggaga ccacagcctc actgcatggc ccaggatgga    8820
cctggtgggt ggatgcaggg cgctcaggct ggagctggga gaggcagggg ctgggtggag    8880
ctgcctgccc ctgtgttcca gtctagatgg gcagagggaa aggtgtgagc atcctccctg    8940
cctgggggtc ttggggacta gtgtagactt gtccaggaac tgtgtaggtg tagatggggc    9000
atgtgttgca ccaaccttgg tcttggggag caaaggttgg gcttgttggc attgcctctc    9060
ggcctccctg gcccttttgcc tcctgggcag ggccgtctga ctgccgaccc caatcctagc    9120
cagcttgcct tgggtgccct gagggcgtct gcctcatggg gctcctgcca tggctctcag    9180
```

```
gcccactctc cctgcctagg ggctctgagg ggcagatgtg cgtgtgcggg agggaaaggg    9240
aggctctggc ctctcctctt acaaagttga ggacttgctc aatgctgtgt gtggtgtccc    9300
agtggcacgg cagatggggg gtgaggcggg cctgcagcta gtgtatatga gccagcactg    9360
cttcctagga cgtgtgggggg cctggccaag ctcttgctgt ccttgtccta actatatggc    9420
agtccctcta ttgggctggg tgccctcttc cacctgtgca gtatgctgag gaccaggcag    9480
ggtctgcctg tgcccctcca gcgctggttg ggagatcatg ggtgggtgcc tgcctctgtt    9540
ggaagcctct cagccagcag gcacctagcc ccgggtgggt tcctttcagc cccctcagcc    9600
tgggcacaca tcacaaacaa gtggaggcta cactggcaca cgagggctgg atccctgcct    9660
ctgggaaagt gcatgtcagg ctggtgtgtg gctggcgcct ggcctgcctt tgccagtttg    9720
agcctgcacg tccaagtgtg gggacccctt agttcccggg tgctgggatg gccaactga     9780
atatggtgga ctcaaccctc accacttggt ccccacagtg ctgggcagtg ccccctggtc    9840
catccccagg ttggaccctg cttgtggccc cagtgctagt ccacagccag agtacatggc    9900
agtggccaga ggcctctgga gagtgaggcc tggagtgtcc aagctccatg taggtccagt    9960
ccgggcaggg ccagctgggc ttgcttctga ccctgacatg ctcgtcccgc tgcctggagg   10020
tgcaggctct gggggtccgg agagctttgc ccactgtagg tcttgaggcc acagtgtggc   10080
tctgcctggc ttctcctcct ggttgtaaat aaggagtggg gcctgagggc agacgaggac   10140
actggggtgg gggcctggat cctgcggggg tggcgctgcc ctgctggtgc ccactcaggg   10200
ggtgcttgtg ttgtgctctg tcaggtgcca tcgcctgcag gattctttat tcagctctga   10260
cagtggcttc agcaactacc gtggcatcct gaactggtgt gtggtgatgc tggtgagtgg   10320
gacatggtgt cgggagcggg tctaggtcca ggtggggctc tgtcccaggc tggcctttgc   10380
ctgagaacag gctctgtcac ccagggtgtc caggctggag ccctgtggg ctggggtgtg    10440
tggagcaggc tgcacctcca tgtgctgcc agcactggac tgttggggag gggagtggca    10500
gtggctgccc ctgctgtggt cacttgggtg cccatgcacc acatacttgc tgcttcccat   10560
tggatcccag gaaaaccctg ctgatgtggt gtgggcgtgg ggacgccgaa caatgcctgg   10620
ctggaacctg tgtgttgtga gctgggcctg aggggtgcag ggcctccagg gagggcaggg   10680
tggaggggggt cttgccctgg gctggtggga gagtggactg catgctctgt ggacacaagg  10740
cctctctggc aggggatgtg agaagagctt cctgtgctac gccacatggc ctctgtgggt   10800
atggagccct gcaggcctgg ccaccactct gcagtcctcc tggcccctt cctcagctgt    10860
gggtcctagg agccccccag gaaagtgatt agatggagcc ctgtgccacg tccaaggcct   10920
gctacctctg ggcctggttc ccactgnnnn nnnnnnnnnn nnnnnnnnnn nnnnnnnnnn   10980
nnnnnnnnnn nnnnnnnnnn nnnnnnnnnn nnnnnnnnnn nnnnnnnnnn nnnnnnnnnn   11040
nnnnnnaccc cagaagtagt tggagtttag ggctcaaagg ggcacctgca gggcaggtcg   11100
gggacaaggg ctatctgggc ccagcctccc caactcaggg ctgatgtggc tcgaggcctt   11160
tgaccttcac ccaggcgtgt ctatctctgg ccttgggtgc tgctcctgtg gctacccacg   11220
tggaagggggc tccacgcaca tccacatccc ccaccgccca tggtcctaga aggttccctg   11280
ggggtggcca gctgtggagg cccacgagtc ctggtggctg agaagctggc caggcaggag   11340
gacagtgggc ccagcgccag cccagcactc aggagacgca gcccattcct ggcccaggtt   11400
gggccttgtc cagcccaggc agcactgtgt attctcccca accccttggg cctgcctggc   11460
cctttggccc atcactgaag ccttttcct gctttggctc ccccttgccc ccaccccaag    11520
catgtatccc gctctgggct gcttgttgca ttccttctgt ggcctgggcc tggaggtggg   11580
```

```
taccatccat tggcaacttt ggcttctgcc tgctgtcaac cctcaggaga agccagtgac   11640
agtgtgggcc acgtgtccat gcagaaggcc tgtgtgtcag ccctgcggcc ggggaggcg    11700 gggcagtagc ccttgtgtct ctgaagcagt cttctctctc atgaagcctt ccctgaccac   11760
ccaggcaaga caccctcagt gttcccttgc cagcgaccct tttccccagc accagttcac   11820
taccgcatga ggcccgagct ccgggtggtc agccaggtct gcggcattgg ggcccagctt   11880
aatggaggtg ttggtagtgc ttgtaagatg gaggaggagg ttcctgtcct tgcagaggga   11940
ggccaagcac ccaactccag gctcgtccca agagccttat tccatggggg ctcagtcctg   12000
ggaagttgct ttggagccaa gtgtccaagg cttagagggc ggcaggaagc agaagaggca   12060
ggcggggcac aagccctggg aagcactcca ggcccagccc ccttgcgac acagctggac    12120 actgctcctg cagagaaaga gtagacaact ccccctcttc agccttggcc accagtaggg   12180
actggttcct tggggctcag ccgtgggcag gcctcctgg gcaggcctgt attctggggc    12240
tgtctctggg gtgtggttgg ctgtgggagc cttgggtccc tcactggctc ggctcagcag   12300
gagggatgtg agcagatcag cagctggtct ttctgctcct gaagacccag gcgtctggca   12360
gggttggttg gtctggccgg ttggttccct ccatgtggga ccgtctggtg tgatgggac    12420 agggagggac ttcccttac ccagcactgg tgttggctga ggtgggtgct gagtctcaga    12480
gcttggcatg gagaccagac agggctgggt ctgcaagcct gaggctgccg ccctgagctc   12540
gggctgggac gtgcccagag gtgttgggag gatctggggt gagtaccctg tggccaggac   12600
taaaggggct gcaccctcct gtccatccct cgcagatctt gagcaatgcc cggttatttc   12660
tggagaacct catcaagtga gtgcctttgc caggtcccac ccctgcccca cccatggcct   12720
gtccaggccc cgccccacag ccccacctgc cacccaatca gaccccccatc cctccacccc   12780 caggtatggc atcctggtgg accccatcca ggtggtttct ctgttcctga aggatcccta   12840
tagctggccc gccccatgcc tggttattgg tgagctgggc tctgaggagg gcctcgggtg   12900
gggatcaggc tgacgtggcc ctaaacctgc cccttggtgc ttctgtccac agcggccaat   12960
gtctttgctg tggctgcatt ccaggttgag aagcgcctgg cggtggtaag cagtgcccct   13020
cacctccgtg tgtgctcacc ctgctgtgtg cgctcctggg aggagctgct ccccaggcct   13080
ggcagccctc tcccaggcaa tgggagccct ggttgagtgc tctgctcccc actccagggt   13140
gccctgacgg agcaggcggg actgctgctg cacgtggcca acctggccac cattctgtgt   13200
ttcccagcgg ctgtggtctt actggttgag tctatcactc caggtgcgcc cccatcccac   13260
cctgcccatc tgtctcgggc cagccacggg catggcctcc ggctgtggcg ctgtggaggc   13320
ctgagtccac ctctcctgca gtgggctccc tgctggcgct gatggcgcac accatcctct   13380
tcctcaagct cttctcctac cgcgacgtca actcatggtg ccgcagggcc agggccaagg   13440
ctggtgaggg gctgccaggg gctggggctg cctgctgggg ggctgggcag cagcagggcc   13500
ccaccagccc cctcccactc tgctgtgctc gtagcctctg cagggaagaa ggccagcagt   13560
gctgctgccc cgcacaccgt gagctacccg acaatctga cctaccgcgg tgaggacctc    13620
tgtgggcctg aggtgcgggg gacaggctgg gcctgttctg gtaccaaccc cccattccca   13680
ttccagatct ctactacttc ctcttcgccc ccaccttgtg ctacgagctc aactttcccc   13740
gctctccccg catccggaag cgctttctgc tgcgacggat ccttgagatg gtgaggttgg   13800 gggtggggg cagccactgg aggctagggg gccttctggc tagccagggc ctcagctggc    13860
tgctctctgt ttcccccca gctgttcttc acccagctcc aggtgggct gatccagcag     13920 gtaagtgggg tagggcaggg ttgggtgtag ctgggcatgg ctgggagctg acgtggtgcc   13980
```

```
ctcctttgca gtggatggtc cccaccatcc agaactccat gaagcccttc aaggtgagtg   14040
gctcaggtgc tcttgcagct gggtggctg gggagtgacc aggagcatgg ctagctgaag   14100
ggcttgtttc tgcaggacat ggactactca cgcatcatcg agcgcctcct gaagctggcg   14160
gtgagtgcgg acaggtggcg catgcacagg acaggagggg acagtggcat gtggggaag   14220
gttctagaac ttggtgccca ccccacctc cctgccaggt ccccaatcac ctcatctggc   14280
tcatcttctt ctactggctc ttccactcct gcctgaatgc cgtggctgag ctcatgcagt   14340
ttggagaccg ggagttctac cgggactggt ggtgagtgtc cctggggtgt ccctggggc   14400
tgggatgggc catggtgtgc tctgatcccc ctgtggtctc ttggcccca ggaactccga   14460
gtctgtcacc tacttctggc agaactggaa catccctgtg cacaagtggt gcatcaggta   14520
ggtgggggtgt gtgtgtgtgt gatgtggaac atggctgtga acctgaaccg cttccatgc    14580
cccctcctct gcagacactt ctacaagccc atgcttcgac gggcagcag caagtggatg    14640
gccaggacag gggtgttcct ggcctcggcc ttcttccacg aggtcagtgc tctgggggc   14700
atcttgcctc atccctgggc aggggtatgc ccacagcagg gacggctgac accccactcc   14760
ctggcatcct ctctccctcc catctcagta cctggtgagc gtccctctgc gaatgttccg   14820
cctctgggcg ttcacgggca tgatggctca ggtgagtgac cccacgtgg cctcctcact    14880
cgcccagtta ccccgcacct gaaccccctcg gctgacccc cccatgccca gggaccctga   14940
agccccagc cctgtggtca ccatggccga ctgacttggc ccctcactcc ctagatccca   15000
ctggcctggt tcgtgggccg cttttttccag ggcaactatg gcaacgcagc tgtgtggctg   15060
tcgctcatca tcggacagcc aatagccgtc ctcatgtacg tccacgacta ctacgtgctc   15120
aactatgagg ccccagcggc agaggcctga gctgcacctg agggcctggc ttctcactgc   15180
cacctcacac ccgctgccag agcccacctc tcctcctagg cctcgagtgc tggggatggg   15240
cctggctgca cagcatcctc ctctggtccc agggaggcct ctctgcccct atggggctct   15300
gtcctgcacc cctcagggat ggcgacagca ggccagacac agtctgatgc cagctgggag   15360
tcttgctgac cctgccccgg gtccgagggt gtcaataaag tgctgtccag tgacctcttc   15420
agcctgccag gggcctgggg cctggtgggg ggtatggcca cacccacaag ggcgagtgcc   15480
agagctgtgt ggacagctgt cccaggacct gccggggagc agcagctcca ctgcagcagg   15540
gcgggcatgg ccgtaggggg gagtgcaagg ccaggcagac gccccattc cccacactcc    15600
cctacctaga aaagctcagc tcaggcgtcc tctcctggtg ctactcctgc tgggtgtgcg   15660
ggaatcggca ctctggccct cagtgcagga tggtcaactt gcaccaccg tgctcagctt    15720
cagcttggga agaggtcggc cctgggtttg cgggaagtgg gctccagcca ggatggccca   15780
gggatggca gtccacaggg ccttttctggt gtgggtctgg tgagccgagg gctacggta    15840
cacaatggct atgtccatgg ctattcgcct tgggggcaggg ctcggtttgg cagcctcttt   15900
ccttcacttg gaacctgggc agccaggtgg gctggtggct ctcagctgcc ctccacgagg   15960
ttggggcacc cctgatcccc aggcctgcct tgccctctac tcttctggca ccaggctggg   16020
cagtgcagac agcgcagccc tgcagccttc aggacacctt gttcccaggc cctgcaatcc   16080
accaagctgg atagatgggg ccccccttga tggtagcggg aggtcagggg taaccccagg   16140
gccctgctgt tgccttacct tgctggggtg actgcttgat taaagacccc aagactggac   16200
caggccctgg tgtccccaga cctgcagcta tggcccaaca aggcaggtgt ttgaggaggc   16260
cctgcacagg gtcccaggac tgcaccaggg gcctcatcag caacctgctg aactggtggt   16320
gtgaggggag ggtgggctcc cttggtggta tcctccctct accccagtgg gggctggtgg   16380
```

```
gccctgagat ggaggcatct ccttgggccc tgctgaggat ggcagtagtg ggtgagctcc    16440 tggtggggg atgggtgtgg ggccgactcc tccatcccac atgggctcct gtgcctctcc    16500
ctatcagttg gccagtggag ctcgagaaca aactgttgct gccagataaa gcagcaaagc    16560
ctgctccact gcccagcgca gccccctttc ccttcctcca ccaggctgag tggagaaccc    16620
taaagctacg ggacaggctc ccgttccccg tgcctacaca gggtgctggc tctggcagaa    16680
agacagtgtg cccgccccgc atcacctgtc cgagtgcgaa caccttggga aggggttcc    16740 tggtggtcct gtgacaacca gagaccccca gggccaaggt gaggcgccca cccctggtcc    16800
ctcaataaag aactgcaagc acatgctggt cctggggagt cgggcaggca cggagctagc    16860
tgcaagcatc cgtcttcccc caggaggcca ctgcagcccg gcccttctgt gccctgggcc    16920
cctcctcatt gcagcaccac ccaccgcacc accctgggac agaggaaaca catggaggcc    16980
atagcataga gcctgtctgt ttatagatct ctgcctgtct tgtccgtcca tccactgtgt    17040
gtatatatct gtgtatctct gtggagcggg gaacgggaca gttgtgtaaa aatccaaaat    17100
acaattctga ctatgaacaa cctgcagggt cagtccaggt gtggctgtga agccccaacc    17160
aaaccacagg acacggggtt gggggaaggc agactggcag gccagggtga ccctcctgac    17220
cagaggtgct gcccagaccc gagcccgttt gtcctactgg ggctatggcg gccgacccac    17280
cagtgcccaa gaccgcgagg ctgccctgcc tccccaagac cagccctgca ctggggggtgg    17340 gggtgggcgg ctggcccagc tcctccgggg cctctaggag acagtggggt ccttggcttt    17400
gggaggctcc gagcctgtca gcagggagat ggtggggtcc tcggcgaagc cgtcccttc    17460 ggagaagtag gagccctctc ccagctcaaa cagcaccggc aggtcgttgc tcccggtgtc    17520
cacggagccg gggtccagca ggaacagcgg ctgcgctgtg tagtgcacca gctgcttccc    17580
tgcgggggtg ggggtgtcaa ggcggtgggg ggttgggggc agaggtgggg ccggtgggac    17640
ttggctcacc tgaatccggg ctgctgttct ctgcctcggg aggcctgggg ggctcctggg    17700
gagacaggag ctcttggatc tgtggggtgg agacggtatt gtgagcactc ccgctggtct    17760
cgttccccct caccccccgc ccgcctacgc acactggcca ggctgctgtc aaggtcaggc    17820
aggctcatgt cgggcacggt caccgagggg ctgaacagct cgcggaggagg gagggaagtc    17880 agaacagcac ccgggggcgg ggcggggaag cggggaggcg gggaggcggg cgggggaggc    17940
ggggaggcgg cgcggggagg cggggaggcg gcgcggggag gcggggaggc ggcgcgggga    18000
ggcggggagg cggggaagcg cggggaggcg gggcggggag gcggggcggc ggggctccac    18060
tcacgtccag cagggcactg gtgtccacgc tgaagccgtg gctgctcagc atggtctgca    18120
ggttatccag gttggagtcc atagcatcca agtggtcact gagctcattc ctggcccggg    18180
ataaggcggt acctgaacca gtgccccagg ccccacaccc caatgccctc ctgtgggaga    18240
agggctcccc ttgactgtac cccccaggct gcaccccgt gtacgcctgc acaggctgga    18300 ggggcagcg cattcgagga cggcctgaa ggcagtggag gctctgtgcc ctgcaggggt    18360
gcggctgggc ctatgatggg catcccttttg ccatgagggc ctgggggcct tggtggcagt    18420
ggacccagga gacaagggc gtattcagct ccagcacaag gatcagggat ttcagtgttc    18480
agggttggtg aggtttcccg ttgcactggg aaaacaggtg gggctctgct cagtgtgtgg    18540
gtggctcagt ccctgccctg gtgctgctgt ggggatgaga cccacggtct ggtggctgtg    18600
accaagaaag ccctaggcca cagggcacac ctgggctatg ggacggacag ccaggctggg    18660
tcccagaggt gccctggaga ccctgcctga caggaagtgc agtcagcacc gcagtctgga    18720
tcctgccaac accagaggcc gtgccagagc agggaggcct gtccctgtca tccctgtcac    18780
```

| | |
|---|---|
| aggcaatgac cacaggcccg tggccagggg agccatgacg acactgagcc cccgccacag | 18840 |
| aggggtctcg gctgctgccg cccaggcccg acgctcatgc ccggccaggc tgggtctggt | 18900 |
| ccacggctgt gtgggagggc ccgagcgctg gcagagccct cctccctccc cagtggggtc | 18960 |
| agcgctaacc ctggctggac ttggccatgc ggagaggaag aggggcaggg gaagaggcgg | 19020 |
| gcgaccctag acatctgtgg agtgcgagcc aaactgcaag atacaaaaac aagagccccc | 19080 |
| attgcaggca ggggctgggg gtgtggaggc cggccctgct caccatctcc tgccatgtgt | 19140 |
| ctgggcagca cgacctgcca gggcccgtgg cctgtggcga gggtggcggc agcaggaggg | 19200 |
| gtggctgaga gcagggcccg gcagcctgtc cggacatgcc cgtggcttct gtggcgtttg | 19260 |
| ggactgtggg gtgatctggc tggcacctgt ctccctcccc agccccgagc tccgaggttg | 19320 |
| ggggtagggt cctgcctcgc cagctgccct gctcagtcca ctgggacagt cggggctgaa | 19380 |
| gcccagggct gtgcgtccag gcgctgtggg tggggccagg ggtgggcggc actcacttgt | 19440 |
| ccaggcaggc taccctgaag cacttttcat gggtggaggt gggcggggg gaaggaagcc | 19500 |
| ggccctcggt gtccgtgtgg cccctggcgt ccgtgagggc tgtgacggag gcggggcag | 19560 |
| gttcactctc ccgcaggatg gagtcaatga gggcggtcgg ggacaagagg gtgtccacgg | 19620 |
| aagatgggcg cccgggactc gcctcctcta cccgggggct ctgaggcggg ctgggggct | 19680 |
| cctccttgac acgcaccagg gggctgctgg ataggggcct gcacgcgagg ggggccaggt | 19740 |
| gagctggcgt ctcggccagc cccacctcat ccccaactct gccctgggcc cacaggggct | 19800 |
| cgcctcattg ggggacagga tggctggggt gatgcggccc ccacctctcg tctatgctcc | 19860 |
| cgccggggga ggccatgggg ctggcaggag ccagctcggt gatgtcggag atgatgggtc | 19920 |
| cagagctggc cacagcatca ggggcgtaga ggctggagct gctgtaggct ggggagggg | 19980 |
| cctgcaatca aaggcaggag gtccatgcag tgccggcagg ggcaacccac cccactgccg | 20040 |
| cctgcatgcc tggcgggtg ccctgtctcc ggcactcacc gagtaggggc ccgagccgtg | 20100 |
| gacgtgctcc agggagaact gccggctata cttgggcatg gaatgtgctg agccactgtc | 20160 |
| gttcagcatc aggggctgt ggggaagggt gcaggtcagc caccacccc cacctcgggg | 20220 |
| tacccggggc acagctgaca gagaaggggg acagccctgg gccccgggtg gtggatgcag | 20280 |
| gcatccccaa aacctcacat ctttctcttc accccagga tccggtttga ctgcaccagt | 20340 |
| gagatcagga actgaatgag ctgtggagag agaggacaca gttaccccgg cccttgtggg | 20400 |
| gcccccgccg gccctctggc cctgccccca ccttgttgac gactttctgt tgctgggcat | 20460 |
| gcttctgccg aaggctggcc acctcccgcc acagagcctc attctcactg caacagacca | 20520 |
| ggctgggtca gtggggccca atcccatgag ccccagggct gagggagccc cacagaccct | 20580 |
| ccctgtcccc catgcaggag caggggtaag tgtgaccatg tctggcctgg cccacccag | 20640 |
| gatgagaact tgtgtgtgga gggactgggg gccagggcca gggcttgctg gtcccactgc | 20700 |
| ccctccctgc cggggacacc tggtgtcacg tagggtgttg gggatggatc catgcgagcc | 20760 |
| aggtgcaccc ggatcctggc atccatcctg gcaaacacct ggagggctgc cttggacaca | 20820 |
| ggccaggagc agacccttgg gccgcccttc caaggcctga gcagccaggt taagggagga | 20880 |
| cggttcttca ggctgcgaca ctggctgtcc catgtcctgt aggtgctcag ggccctcgcc | 20940 |
| aggcctggag gtggctcagg ggtggggaag agctgtcccc agccaggtga gcagggccat | 21000 |
| g | 21001 |

<210> SEQ ID NO 4
<211> LENGTH: 1976
<212> TYPE: DNA

<213> ORGANISM: Homo sapiens

<400> SEQUENCE: 4

```
gaatggacga gagaggcggc cgtccattag ttagcggctc cggagcaacg cagccgttgt    60
ccttgaggcc gacgggcctg acgcgggcgg gttgaacgcg ctggtgaggc ggtcacccgg   120
gctacggcgg ccggcagggg gcagtggcgg ccgttgtcta gggcccggag gtggggccgc   180
gcgcctcggg cgctacgaac ccggcaggcc cacgcttggc tgcggccggg tgcgggctga   240
ggccatgggc gaccgcggca gctcccggcg ccggaggaca gggtcgcggc cctcgagcca   300
cggcggcggc gggcctgcgg cggcggaaga agaggtgcgg gacgccgctg cgggccccga   360
cgtgggagcc gcggggacg cgccagcccc ggcccccaac aaggacggag acgccggcgt   420
gggcagcggc cactgggagc tgaggtgcca tcgcctgcag gattctttat tcagctctga   480
cagtggcttc agcaactacc gtggcatcct gaactggtgt gtggtgatgc tgatcttgag   540
caatgcccgt ttatttctgg agaacctcat caagtatggc atcctggtgg acccatccag   600
ggtggttttct ctgttcctga aggatcccca tagctggccc gccccatgcc tggttattgc   660
ggccaatgtc tttgctgtgg ctgcattcca ggttgagaag cgcctggcgg tgggtgccct   720
gacggagcag gcgggactgc tgctgcacgt agccaacctg ccaccattc tgtgtttccc   780
agcggctgtg gtcttactgg ttgagtctat cactccagtg ggctccctgc tggcgctgat   840
ggcgcacacc atcctcttcc tcaagctctt ctcctaccgc gacgtcaact catggtgccg   900
cagggccagg gccaaggctg cctctgcagg gaagaaggcc agcagtgctg ctgccccgca   960
caccgtgagc tacccggaca atctgaccta ccgcgatctc tactacttcc tcttcgcccc  1020
caccttgtgc tacgagctca cttttcccg ctctccccgc atccggaagc gctttctgct  1080
gcgacggatc cttgagatgc tgttcttcac ccagctccag gtgggctga tccagcagtg  1140
gatggtccc accatccaga actccatgaa gcccttcaag gacatggact actcacgcat  1200
catcgagcgc ctcctgaagc tggcggtccc caatcacctc atctggctca tcttcttcta  1260
ctggctcttc cactcctgcc tgaatgccgt ggctgagctc atgcagtttg gagaccggga  1320
gttctaccgg gactggtgga actccgagtc tgtcacctac ttctggcaga actggaacat  1380
ccctgtgcac aagtggtgca tcagacactt ctacaagccc atgcttcgac ggggcagcag  1440
caagtggatg gccaggacag gggtgttcct ggcctcggct ttcttccacg agtacctggt  1500
gagcgtccct ctgcgaatgt tccgcctctg ggctttcacg ggcatgatgg ctcagatccc  1560
actggcctgg ttcgtgggcc gcttttttcca gggcaactat gcaacgcag ctgtgtggct  1620
gtcgctcatc atcggacagc caatagccgt cctcatgtac gtccacgact actacgtgct  1680
caactatgag gccccagcgg cagaggcctg agctgcacct gagggcctgg cttctcactg  1740
ccacctcaaa cccgctgcca gagcccacct ctcctcctag gcctcgagtg ctggggatgg  1800
gcctggctgc acagcatcct cctctggtcc caggaggcc tctctgccct atggggctct  1860
gtcctgcacc cctcagggat ggcgacagca ggccagacac agtctgatgc cagctgggag  1920
tcttgctgac cctgccccgg gtccgagggt gtcaataaag tgctgtccag tgggag       1976
```

<210> SEQ ID NO 5
<211> LENGTH: 170
<212> TYPE: DNA
<213> ORGANISM: Homo sapiens

<400> SEQUENCE: 5

```
cgcctcaggt cggccgcgga ctacaaatgg acgagagagg cggccgtcca ttagttagcg    60
```

| | |
|---|---|
| gctccggagc aacgcagccg ttgtccttga ggccgacggg cctgacgcgg gcgggttgaa | 120 |
| cgcgctggtg aggcggtcac ccgggctacg gcggccggca gggggcagtg | 170 |

<210> SEQ ID NO 6
<211> LENGTH: 913
<212> TYPE: DNA
<213> ORGANISM: Homo sapiens
<220> FEATURE:
<221> NAME/KEY: misc_feature
<222> LOCATION: 913
<223> OTHER INFORMATION: n = A,T,C or G

<400> SEQUENCE: 6

| | |
|---|---|
| gcttggctgc ggccgggtgc gggctgaggc catgggcgac cgcggcagct cccggcgccg | 60 |
| gaggacaggg tcgcggccct cgagccacgg cggcggcggg cctgcggcgg cggaagagga | 120 |
| ggtgcgggac gccgctgcgg gccccgacgt gggagccgcg gggacgcgc cagccccggc | 180 |
| ccccaacaag gacggagacg ccggcgtggg cagcggccac tgggagctga ggtgccatcg | 240 |
| cctgcaggat tctttattca gctctgacag tggcttcagc aactaccgtg gcatcctgaa | 300 |
| ctggtgtgtg gtgatgctgg tatggcatcc tggtggaccc catccaggtg gtttctctgt | 360 |
| tcctgaagga tccctatagc tggcccgccc catgcctggt tattgcggcc aatgtctttg | 420 |
| ctgtggctgc attccaggtt gagaagcgcc tggcggtggg tgccctgacg gagcaggcgg | 480 |
| gactgctgct gcacgtggcc aacctggcca ccattctgtg tttcccagcg gctgtggtct | 540 |
| tactggttga gtctatcact ccaggggcgc cccatcccca cctgcccat ctgtctcggg | 600 |
| ccagccacgg gcatggcctc cggctgtggc gctgtggagg gctgagtcca cctctcctgc | 660 |
| agtgggctcc ctggtggcgc tgatgggca caccatcctc ttcctcaagc tcttcttcta | 720 |
| ccgcgacgtc aactcctggg ggccccaggg cccaggccca aggttgcctc tggcagggaa | 780 |
| aaagggccag cagtgctgc ctggcccgca accggggga ggtaccccgg accaatttgg | 840 |
| acctcccgcg gatctccaag aacttcccgc cttgcgcccc ccctgggg ggtagcgagc | 900 |
| ttaacttttt gcn | 913 |

<210> SEQ ID NO 7
<211> LENGTH: 1650
<212> TYPE: DNA
<213> ORGANISM: Mus musculus

<400> SEQUENCE: 7

| | |
|---|---|
| ggatgaatgg aaataagtag aattaggcat acttaggata gggctcaagc cgcggcccgt | 60 |
| gaagattggg ccgcgacgag gtgcgggccg aagccatggg cgaccgcgga ggcgcgggaa | 120 |
| gctctcggcg tcggaggacc ggctcgcggg tttccgtcca gggtggtagt gggcccaagg | 180 |
| tagaagagga cgaggtgcga gacgcggctg tgagccccga cttgggcgcc gggggtgacg | 240 |
| cgccggctcc ggctccggct ccagcccata cccgggacaa agacgggcgg accagcgtgg | 300 |
| gcgacggcta ctgggatctg aggtgccatc gtctgcaaga ttctttgttc agctcagaca | 360 |
| gtggtttcag caattatcgt ggtatcctga attggtgtgt ggtgatgctg atcctgagta | 420 |
| atgcaaggtt atttttagag aaccttatca agtatggcat cctggtggat cctatccagg | 480 |
| tggtgtctct gttttttgaag gaccoctaca gctggcctgc cccatgcgtg attattgcat | 540 |
| ccaatatttt tgttgtggct gcatttcaga ttgagaagcg cctggcagtg ggtgccctga | 600 |
| cagagcagat ggggctgctg ctacatgtgg ttaacctgc cacaatcatt tgcttcccag | 660 |
| cagctgtggc cttactggtt gagtctatca ctccagtggg ttccgtgttt gctctggcat | 720 |

-continued

| | |
|---|---|
| catactccat catgttcctc aagctttatt cctaccggga tgtcaacctg tggtgccgcc | 780 |
| agcgaagggt caaggccaaa gctgtctcta cagggaagaa ggtcagtggg gctgctgccc | 840 |
| agcaagctgt gagctatcca gacaacctga cctaccgaga tctctattac ttcatctttg | 900 |
| ctcctacttt tgtgttatgaa ctcaactttc ctcggtcccc ccgaatacga aagcgctttc | 960 |
| tgctacgacg agttcttgag atgctctttt ttacccagct tcaagtgggg ctgatccaac | 1020 |
| agtggatggt ccctactatc cagaactcca tgaagccctt caaggatatg gactattcac | 1080 |
| ggatcattga gcgtctctta aagctggcgg tccccaacca tctgatctgg cttatcttct | 1140 |
| tctattggtt tttccactcc tgtctcaatg ctgtggcaga gcttctgcag tttggagacc | 1200 |
| gcgagttcta cagagattgg tggaatgctg agtctgtcac ctacttttgg cagaactgga | 1260 |
| atatccccgt gcacaagtgg tgcatcagac acttctacaa gcctatgctc agacatggca | 1320 |
| gcagcaaatg ggtggccagg acaggagtat ttttgacctc agccttcttc catgagtacc | 1380 |
| tagtgagcgt tcccctgcgg atgttccgcc tctgggcatt cacagccatg atggctcagg | 1440 |
| tcccactggc ctggattgtg ggccgattct tccaagggaa ctatggcaat gcagctgtgt | 1500 |
| gggtgacact catcattggg caaccggtgg ctgtgctcat gtatgtccac gactactacg | 1560 |
| tgctcaacta cgatgcccca gtgggggtat gagctactgc caaaggccag ccctccctaa | 1620 |
| cctgggcctg gagttctgga ggggttcctg | 1650 |

<210> SEQ ID NO 8
<211> LENGTH: 490
<212> TYPE: DNA
<213> ORGANISM: Mus musculus

<400> SEQUENCE: 8

| | |
|---|---|
| gtattttga cctcagcctt cttccatgag tacctagtga gcgttcccct gcggatgttc | 60 |
| cgcctctggg cattccagcc atgatggctc aggtcccact ggcctggatt gtgggccgat | 120 |
| tcttccaagg gaactatggc aatgcagctg tgtgggtgac actcatcatt gggcaaccgg | 180 |
| tggctgtgct catgtatgtc cacgactact acgtgctcaa ctacgatgcc ccagtggggg | 240 |
| tttgagctac tgccaaaggc cagccctccc taacctgggc ctggagttct ggaggggttc | 300 |
| ctggctgcct gcacactcct cctagtttgg gaggcctctc tgcccctatg ggcctactc | 360 |
| ctgctcttgg ggatggcatt tgaatctcag cactggtatg agccagtgct gggagtctgt | 420 |
| gttgtccagg ggctgagggt atcaataaag tgctgtctaa acccttaaaa aaaaaaaaa | 480 |
| aaaaaaaaaa | 490 |

<210> SEQ ID NO 9
<211> LENGTH: 1776
<212> TYPE: DNA
<213> ORGANISM: Mus musculus

<400> SEQUENCE: 9

| | |
|---|---|
| agcacgactg ggccgcgacg aggtgcgggc cgaagccatg gcgaccgcg gaggcgcggg | 60 |
| aagctctcgg cgtcggagga ccggctcgcg ggtttccgtc cagggtggta gtgggcccaa | 120 |
| ggtagaagag gacgaggtgc gagacgcggc tgtgagcccc gacttgggcg ccggggggtga | 180 |
| cgcgccggct ccggctccgg ctccagccca tacccgggac aaagacgggc ggaccagcgt | 240 |
| gggcgacggc tactgggatc tgaggtgcca tcgtctgcaa gattctttgt tcagctcaga | 300 |
| cagtggtttc agcaattatc gtggtatcct gaattggtgt gtggtgatgc tgatcctgag | 360 |
| taatgcaagg ttatttttag agaaccttat caagtatggc atcctggtgg atcctatcca | 420 |

```
ggtggtgtct ctgtttctga aggacccta cagctggcct gccccatgcg tgattattgc      480
atccaatatt tttgttgtgg ctgcatttca gattgagaag cgcctggcag tgggtgccct      540
gacagagcag atggggctgc tgctacatgt ggttaacctg ccacaatca tctgcttccc      600 agcagctgtg gccttactgg ttgagtctat cactccagtg ggttccgtgt ttgctctggc      660
atcatactcc atcatgttcc tcaagcttta ttcctaccgg gatgtcaacc tgtggtgccg      720
ccagcgaagg gtcaaggcca aagctgtctc tacagggaag aaggtcagtg gggctgctgc      780
ccagcaagct gtgagctatc agacaacct gacctaccga gatctctatt acttcatctt      840
tgctcctact ttgtgttatg aactcaactt tcctcggtcc cccgaataca gaaagcgctt      900
tctgctacga cgagttcttg agatgctctt ttttacccag cttcaagtgg ggctgatcca      960
acagtggatg gtccctacta tccagaactc catgaagccc ttcaaggata tggactattc     1020
acggatcatt gagcgtctct taaagctggc ggtccccaac catctgatct ggcttatctt     1080
cttctattgg ttttccact cctgtctcaa tgctgtggca gagcttctgc agtttggaga     1140
ccgcgagttc tacagagatt ggtggaatgc tgagtctgtc acctactttt ggcagaactg     1200
gaatatcccc gtgcacaagt ggtgcatcag acacttctac aagcctatgc tcagacatgg     1260
cagcagcaaa tgggtggcca ggacaggagt attttttgacc tcagccttct tccatgagta     1320
cctagtgagc gttcccctgc ggatgttccg cctctgggca ttcacagcca tgatggctca     1380
ggtcccactg gcctggattg tgggccgatt cttccaaggg aactatggca atgcagctgt     1440
gtgggtgaca ctcatcattg gcaaccggt ggctgtgctc atgtatgtcc acgactacta     1500
cgtgctcaac tacgatgccc cagtggggt ctgagctact gccaaaggcc agccctccct     1560
aacctgggcc tggagttctg gaggggttcc tggctgcctg cacactcctc ctagtctggg     1620
aggcctctct gccccatatgg ggcctactcc tgctcttggg gatggcattt gaatctcagc     1680
actggtatga gccagtgctg ggagtctgtg ttgtccaggg gctgagggta tcaataaagt     1740
gctgtctaaa accttaaaaa aaaaaaaaaa aaaaaa                                 1776

<210> SEQ ID NO 10
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 10
tccgtcatcg ctcctcaggg                                                   20

<210> SEQ ID NO 11
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 11
gtgcgcgcga gcccgaaatc                                                   20

<210> SEQ ID NO 12
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 12
```

-continued atgcattctg cccccaagga                                              20

<210> SEQ ID NO 13
<211> LENGTH: 15
<212> TYPE: DNA
<213> ORGANISM: Artificial Sequence
<220> FEATURE:
<223> OTHER INFORMATION: Forward primer

<400> SEQUENCE: 13
tccccgcatc cggaa                                                   15

<210> SEQ ID NO 14
<211> LENGTH: 22
<212> TYPE: DNA
<213> ORGANISM: Artificial Sequence
<220> FEATURE:
<223> OTHER INFORMATION: Reverse primer

<400> SEQUENCE: 14
ctgggtgaag aacagcatct ca                                           22

<210> SEQ ID NO 15
<211> LENGTH: 22
<212> TYPE: DNA
<213> ORGANISM: Artificial Sequence
<220> FEATURE:
<223> OTHER INFORMATION: Probe

<400> SEQUENCE: 15
cgctttctgc tgcgacggat cc                                           22

<210> SEQ ID NO 16
<211> LENGTH: 19
<212> TYPE: DNA
<213> ORGANISM: Artificial Sequence
<220> FEATURE:
<223> OTHER INFORMATION: Forward primer

<400> SEQUENCE: 16
gaaggtgaag gtcggagtc                                               19

<210> SEQ ID NO 17
<211> LENGTH: 20
<212> TYPE: DNA
<213> ORGANISM: Artificial Sequence
<220> FEATURE:
<223> OTHER INFORMATION: Reverse primer

<400> SEQUENCE: 17
gaagatggtg atgggatttc                                              20

<210> SEQ ID NO 18
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 18
gccgcctctc tcgtccattc                                              20

<210> SEQ ID NO 19
<211> LENGTH: 20
<212> TYPE: DNA
<213> ORGANISM: Artificial Sequence
<220> FEATURE:

```
<223> OTHER INFORMATION: Oligomeric Compound

<400> SEQUENCE: 19
gagccgctaa ctaatggacg                                               20

<210> SEQ ID NO 20
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 20
acaacggctg cgttgctccg                                               20

<210> SEQ ID NO 21
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 21
ccgcccgcgt caggcccgtc                                               20

<210> SEQ ID NO 22
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 22
gcctcaccag cgcgttcaac                                               20

<210> SEQ ID NO 23
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 23
ccctgccggc cgccgtagcc                                               20

<210> SEQ ID NO 24
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 24
ctccgggccc tagacaacgg                                               20

<210> SEQ ID NO 25
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 25
gttcgtagcg cccgaggcgc                                               20

<210> SEQ ID NO 26
```

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 26
cccggccgca gccaagcgtg                                                   20

<210> SEQ ID NO 27
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 27
gcccatggcc tcagcccgca                                                   20

<210> SEQ ID NO 28
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 28
tggctcgagg gccgcgaccc                                                   20

<210> SEQ ID NO 29
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 29
ccgcaggccc gccgccgccg                                                   20

<210> SEQ ID NO 30
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 30
ccgcacctct tcttccgccg                                                   20

<210> SEQ ID NO 31
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 31
acgccggcgt ctccgtcctt                                                   20

<210> SEQ ID NO 32
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 32
```
gctcccagtg gccgctgccc                                                  20

<210> SEQ ID NO 33
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 33
ctgcaggcga tggcacctca                                                  20

<210> SEQ ID NO 34
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 34
aggatgccac ggtagttgct                                                  20

<210> SEQ ID NO 35
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 35
gcatcaccac acaccagttc                                                  20

<210> SEQ ID NO 36
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 36
gccatacttg atgaggttct                                                  20

<210> SEQ ID NO 37
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 37
gacattggcc gcaataacca                                                  20

<210> SEQ ID NO 38
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 38
cttctcaacc tggaatgcag                                                  20

<210> SEQ ID NO 39
<211> LENGTH: 20
<212> TYPE: DNA
<213> ORGANISM: Artificial Sequence
<220> FEATURE:

```
<223> OTHER INFORMATION: Oligomeric Compound

<400> SEQUENCE: 39
gcagtcccgc ctgctccgtc                                               20

<210> SEQ ID NO 40
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 40
caggttggct acgtgcagca                                               20

<210> SEQ ID NO 41
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 41
ccagtaagac cacagccgct                                               20

<210> SEQ ID NO 42
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 42
ggtgtgcgcc atcagcgcca                                               20

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
cagcactgct ggccttcttc                                               20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 44
tgagctcgta gcacaaggtg                                               20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
cactgctgga tcagccccac                                               20

<210> SEQ ID NO 46
```

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 46
atgcgtgagt agtccatgtc                                                    20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
tgagccagat gaggtgattg                                                    20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
gagctcagcc acggcattca                                                    20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
tctgccagaa gtaggtgaca                                                    20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
gatgagcgac agccacacag                                                    20

<210> SEQ ID NO 51
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
ctcatagttg agcacgtagt                                                    20

<210> SEQ ID NO 52
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 52
```

```
cagtgagaag ccaggccctc                                              20

<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53
ccatccccag cactcgaggc                                              20

<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
aggatgctgt gcagccaggc                                              20

<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55
ggtgcaggac agagccccat                                              20

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
gtgtctggcc tgctgtcgcc                                              20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
ctcccagctg gcatcagact                                              20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
ctacttattt ccattcatcc                                              20

<210> SEQ ID NO 59
<211> LENGTH: 20
<212> TYPE: DNA
<213> ORGANISM: Artificial Sequence
<220> FEATURE:
```

```
<223> OTHER INFORMATION: Oligomeric Compound

<400> SEQUENCE: 59
tatcctaagt atgcctaatt                                          20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
gcttgagccc tatcctaagt                                          20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
ctcgtcgcgg cccaatcttc                                          20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
cccatggctt cggcccgcac                                          20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
cagccgcgtc tcgcacctcg                                          20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
cggagccggc gcgtcacccc                                          20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
ccacgctggt ccgcccgtct                                          20

<210> SEQ ID NO 66
```

```
<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 66
cagatcccag tagccgtcgc                                              20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
tcttgcagac gatggcacct                                              20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
tcaggatacc acgataattg                                              20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
cagcatcacc acacaccaat                                              20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
aaccttgcat tactcaggat                                              20

<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
atccaccagg atgccatact                                              20

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
```
agagacacca cctggatagg					20

<210> SEQ ID NO 73
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 73
cagcagcccc atctgctctg					20

<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
gccaggttaa ccacatgtag					20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
aaccagtaag gccacagctg					20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
cccactggag tgatagactc					20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77
atggagtatg atgccagagc					20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
acccttcgct ggcggcacca					20

<210> SEQ ID NO 79
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 79
tggatagctc acagcttgct                                                    20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
tctcggtagg tcaggttgtc                                                    20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
ctcaagaact cgtcgtagca                                                    20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
gttggatcag ccccacttga                                                    20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
gtgaatagtc catatccttg                                                    20

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
taagagacgc tcaatgatcc                                                    20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
tctgccacag cattgagaca                                                    20

<210> SEQ ID NO 86

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
ccaatctctg tagaactcgc                                           20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
gtgacagact cagcattcca                                           20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
gtctgatgca ccacttgtgc                                           20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
tgccatgtct gagcataggc                                           20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
atactcctgt cctggccacc                                           20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
attgccatag ttcccttgga                                           20

<210> SEQ ID NO 92
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 92
```

```
agtgtcaccc acacagctgc                                              20

<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
ccaccggttg cccaatgatg                                              20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
gtggacatac atgagcacag                                              20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
tagttgagca cgtagtagtc                                              20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
ctttggcagt agctcatacc                                              20

<210> SEQ ID NO 97
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 97
tccagaactc caggcccagg                                              20

<210> SEQ ID NO 98
<211> LENGTH: 20
<212> TYPE: DNA
<213> ORGANISM: Artificial Sequence
<220> FEATURE:
<223> OTHER INFORMATION: Probe

<400> SEQUENCE: 98
caagcttccc gttctcagcc                                              20

<210> SEQ ID NO 99
<211> LENGTH: 20
<212> TYPE: DNA
<213> ORGANISM: Artificial Sequence
<220> FEATURE:
```

<223> OTHER INFORMATION: Oligomeric Compound

<400> SEQUENCE: 99
tccatttatt agtctaggaa                                          20

<210> SEQ ID NO 100
<211> LENGTH: 2262
<212> TYPE: DNA
<213> ORGANISM: Mus musculus

<400> SEQUENCE: 100

| | | | | |
|---|---|---|---|---|
| ggtggccgcg | cttcgctggc | tttctgctca | tctagggtgg | cagcggctac | ctacctcagc | 60 |
| tctcgccctg | ctgccgccac | ggcctgggcg | ctgtccctca | gctcccggag | ctcagcgcga | 120 |
| agccctggcc | ccggcggccg | gggcatgggt | caggggcgcg | gcgtgaggcg | gctttctgca | 180 |
| cggccgtgac | gtgcattggc | ttcagcatga | agaccctcat | cgccgcctac | tccggggtcc | 240 |
| tgcggggtga | gcgtcgggcg | gaagctgccc | gcagcgaaaa | caagaataaa | ggatctgccc | 300 |
| tgtcacgcga | ggggtctggg | cgatggggca | ctggctccag | catcctctca | gccctccaag | 360 |
| acatcttctc | tgtcacctgg | ctcaacagat | ctaaggtgga | aaaacagctg | caggtcatct | 420 |
| cagtactaca | atgggtccta | tccttcctgg | tgctaggagt | ggcctgcagt | gtcatcctca | 480 |
| tgtacacctt | ctgcacagac | tgctggctga | tagctgtgct | ctacttcacc | tggctggcat | 540 |
| ttgactggaa | cacgcccaag | aaaggtggca | ggagatcgca | gtgggtgcga | aactgggccg | 600 |
| tgtggcgcta | cttccgagac | tactttccca | tccagctggt | gaagacacac | aacctgctga | 660 |
| ccaccaggaa | ctatatcttt | ggataccacc | cccatggcat | catgggcctg | ggtgccttct | 720 |
| gtaacttcag | cacagaggct | actgaagtca | gcaagaagtt | tcctggcata | aggccctatt | 780 |
| tggctacgtt | ggctggtaac | ttccggatgc | ctgtgcttcg | cgagtacctg | atgtctggag | 840 |
| gcatctgccc | tgtcaaccga | gacaccatag | actacttgct | ctccaagaat | gggagtggca | 900 |
| atgctatcat | catcgtggtg | ggaggtgcag | ctgagtccct | gagctccatg | cctggcaaga | 960 |
| acgcagtcac | cctgaagaac | cgcaaaggct | ttgtgaagct | ggccctgcgc | catggagctg | 1020 |
| atctggttcc | cacttattcc | tttgagagat | gaggtata | caagcaggtg | atctttgagg | 1080 |
| agggttcctg | gggccgatgg | gtccagaaga | agttccagaa | gtatattggt | ttcgcccct | 1140 |
| gcatcttcca | tggccgaggc | ctcttctcct | ctgacacctg | ggggctggtg | ccctactcca | 1200 |
| agcccatcac | caccgtcgtg | ggggagccca | tcactgtccc | caagctggag | cacccgaccc | 1260 |
| agaaagacat | cgacctgtac | catgccatgt | acatggaggc | cctggtgaag | ctctttgaca | 1320 |
| atcacaagac | caaatttggc | cttccagaga | ctgaggtgct | ggaggtgaac | tgacccagcc | 1380 |
| ctcgcgtgcc | agctcctggg | aggacgact | gcagatcctt | ttctaccgag | ttcttgagtg | 1440 |
| cattttgttc | tgtaaatttg | aagcgtcat | gggtgtctgt | gggttattta | aaagaaatta | 1500 |
| taatgtgtta | aaccattgca | atgttagatg | ttttttttaag | aagggaagag | tcagtatttt | 1560 |
| aagctcactt | ctagtgtgtc | ctgctcaagg | tggaggctga | tatttatggg | ccttggtggt | 1620 |
| ttcttaccca | cccccttctag | cgttccccag | acgacagaca | cttggccctg | gctagctggg | 1680 |
| caagggcagt | ccttagtgac | tccagggatt | cttgagaggc | agaggccatg | tcccacccgt | 1740 |
| ggctgcaggt | cgggttcctc | gtaccaaggg | aggctgagg | gcacagctgg | ccccacttgg | 1800 |
| ggagggtaga | taacatctgg | actgcccggc | ttgggtctct | gctcctcacc | ctagccctct | 1860 |
| tctccaatct | gagcctaccc | tggctcctg | tctcctggct | agggacacgg | ctgtcccaca | 1920 |
| ggtgccgtct | tgggttatct | cgctgctgtt | ggctggtttc | actctggagg | ttggcaccat | 1980 |

| | | |
|---|---|---|
| ggacacagct cagcgttgct ctggcgcata tcctcctgag ccacacccca agtctggtgt | 2040 |
| gaggaagggc ttctcttctc ttcacagagg tgcctggctt cctgtgcagc acactgggtc | 2100 |
| caggacagga ggcccccccc ccaaaccaag cctcacgtgt gtgcctttat gaggcgttgg | 2160 |
| gagaaagcta ccctcctgtg tattctgttt tctccatgag attgttgtgc catgtcacac | 2220 |
| ttttgtatat tcctagacta ataaatggaa acaagaacag cc | 2262 |

<210> SEQ ID NO 101
<211> LENGTH: 1751
<212> TYPE: DNA
<213> ORGANISM: Rattus norvegicus

<400> SEQUENCE: 101

| | |
|---|---|
| gaagattggg ccgcgacgag gtgcgggccg aagccatggg cgaccgcgga ggcgcgggaa | 60 |
| gctctcggcg tcgcaggacc ggctcgcggg tttccgtcca gggaggtagt gggcccaagg | 120 |
| tagaagagga cgaggtgcga gaagcggctg tgagccccga cttgggcgcc gggggtgacg | 180 |
| cgccggctcc ggctccggct ccagcccata cccgggacaa agaccggcag accagcgtgg | 240 |
| gcgacggcca ctgggagctg aggtgccatc gtctgcaaga ctctttgttc agctcagaca | 300 |
| gcggtttcag caattaccgt ggtatcctga attggtgcgt ggtgatgctg atcctgagta | 360 |
| atgcaaggtt atctttagag aatcttatca agtatggcat cctggtggat cccatccagg | 420 |
| tggtgtctct gtttctgaag dacccctaca gctggcctgc cccatgcttg atcattgcat | 480 |
| ccaatatctt tattgtggct acatttcaga ttgagaagcg cctgtcagtg ggtgccctga | 540 |
| cagagcagat ggggctgctg ctacatgtgg ttaacctggc cacaattatc tgcttcccag | 600 |
| cagctgtggc cttactggtt gagtctatca ctccagtggg ttccctgttt gctctggcat | 660 |
| catactccat catcttcctc aagctttctt cctaccggga tgtcaatctg tggtgccgcc | 720 |
| agcgaagggt caaggccaaa gctgtgtctg cagggaagaa ggtcagtggg gctgctgccc | 780 |
| agaacactgt aagctatccg gacaacctga cctaccgaga tctctattac ttcatctttg | 840 |
| ctcctacttt tgtgttatgaa ctcaactttc ctcgatcccc ccgaatacga aagcgctttc | 900 |
| tgctacggcg ggttcttgag atgctctttt tcacccagct tcaagtgggg ctgatccagc | 960 |
| agtggatggt ccctactatc cagaactcca tgaagccctt caaggacatg gactattcac | 1020 |
| gaatcattga gcgtctctta aagctggcgg tccccaacca tctgatatgg ctcatcttct | 1080 |
| tctattggct tttccactca tgtctcaatg ctgtggcaga gctcctgcag tttggagacc | 1140 |
| gcgagttcta cagggactgg tggaatgctg agtctgtcac ctactttggg cagaactgga | 1200 |
| atatccccgt gcacaagtgg tgcatcagac acttttacaa gcctatgctc agactgggca | 1260 |
| gcaacaaatg gatggccagg actggggtct tttgggcgtc agctttcttt catgagtacc | 1320 |
| tagtgagcat tcccctgagg atgttccgcc tttgggcatt cacagcaatg atggctcagg | 1380 |
| tcccactggc ctggattgtg aaccgcttct tccaagggaa ctatggcaat gcagctgtgt | 1440 |
| gggtgacact catcattggg caaccggtgg ctgtgctcat gtatgtccac gactactacg | 1500 |
| tgctcaacta tgatgcccca gtgggggcat gagctactgc caaaggccag cctccctaac | 1560 |
| ctgggcctgg agttctggag ggcttcctgc tgctgcacac tcccctagtt tggaggcctt | 1620 |
| tctgccccta tggggcctac tcctgctctt ggggatggcc ctgagccagc tggttgagcc | 1680 |
| agtgctggga gtttgtgctg accaggggct taggatatca ataaagagct atctaaaaaa | 1740 |
| aaaaaaaaaa a | 1751 |

<210> SEQ ID NO 102

```
<211> LENGTH: 16
<212> TYPE: DNA
<213> ORGANISM: Artificial Sequence
<220> FEATURE:
<223> OTHER INFORMATION: Forward primer

<400> SEQUENCE: 102
cagaccagcg tgggcg                                                    16

<210> SEQ ID NO 103
<211> LENGTH: 24
<212> TYPE: DNA
<213> ORGANISM: Artificial Sequence
<220> FEATURE:
<223> OTHER INFORMATION: Reverse probe

<400> SEQUENCE: 103
gaacaaagag tcttgcagac gatg                                           24

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
cggccactgg gagctgaggt g                                              21

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
tcgcccatgg cttcggcccg                                                20

<210> SEQ ID NO 106
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 106
agcttcccgc gcctccgcgg                                                20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
ggtcctgcga cgccgagagc                                                20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
```
ctggacggaa acccgcgagc    20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
taccttgggc ccactacctc    20

<210> SEQ ID NO 110
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 110
tcgcacctcg tcctcttcta    20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
gagccggcgc gtcaccccncg    20

<210> SEQ ID NO 112
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 112
tatgggctgg agccggagcc    20

<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
ccgggtatgg gctggagccg    20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
tcgcccacgc tggtctgccg    20

<210> SEQ ID NO 115
<211> LENGTH: 20
<212> TYPE: DNA
<213> ORGANISM: Artificial Sequence
<220> FEATURE:

-continued

<223> OTHER INFORMATION: Oligomeric Compound

<400> SEQUENCE: 115
ggcacctcag ctcccagtgg                                               20

<210> SEQ ID NO 116
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 116
ctgtctgagc tgaacaaaga                                               20

<210> SEQ ID NO 117
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 117
aggataccac ggtaattgct                                               20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
caccaattca ggataccacg                                               20

<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
gcattactca ggatcagcat                                               20

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
ctaaagataa ccttgcatta                                               20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
acttgataag attctctaaa                                               20

<210> SEQ ID NO 122

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
ccaccaggat gccatacttg                                              20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 123
ggatccacca ggatgccata                                              20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
aaacagagac accacctgga                                              20

<210> SEQ ID NO 125
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
ggatgcaatg atcaagcatg                                              20

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 126
acaataaaga tattggatgc                                              20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
cttctcaatc tgaaatgtag                                              20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
```
aggcgcttct caatctgaaa                                              20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
gctctgtcag ggcacccact                                              20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
agccccatct gctctgtcag                                              20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
accacatgta gcagcagccc                                              20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
gggaagcaga taattgtggc                                              20

<210> SEQ ID NO 133
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 133
aaggccacag ctgctgggaa                                              20

<210> SEQ ID NO 134
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 134
agactcaacc agtaaggcca                                              20

<210> SEQ ID NO 135
<211> LENGTH: 20
<212> TYPE: DNA
<213> ORGANISM: Artificial Sequence
<220> FEATURE:

```
<223> OTHER INFORMATION: Oligomeric Compound

<400> SEQUENCE: 135
tggagtgata gactcaacca                                                    20

<210> SEQ ID NO 136
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 136
ggagtatgat gccagagcaa                                                    20

<210> SEQ ID NO 137
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 137
gaggaagatg atggagtatg                                                    20

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
ccggtaggaa gaaagcttga                                                    20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
ccttcgctgg cggcaccaca                                                    20

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
acagctttgg ccttgaccct                                                    20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
accttcttcc ctgcagacac                                                    20

<210> SEQ ID NO 142
```

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
cagcagcccc actgaccttc                                               20

<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
gatagcttac agtgttctgg                                               20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
ggtaggtcag gttgtccgga                                               20

<210> SEQ ID NO 145
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 145
agagatctcg gtaggtcagg                                               20

<210> SEQ ID NO 146
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 146
aagatgaagt aatagagatc                                               20

<210> SEQ ID NO 147
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 147
acaaagtagg agcaaagatg                                               20

<210> SEQ ID NO 148
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 148
```
aagttgagtt cataacacaa                                              20

<210> SEQ ID NO 149
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 149
aaaaagagca tctcaagaac                                              20

<210> SEQ ID NO 150
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 150
cagccccact tgaagctggg                                              20

<210> SEQ ID NO 151
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 151
catccactgc tggatcagcc                                              20

<210> SEQ ID NO 152
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 152
ggagttctgg atagtaggga                                              20

<210> SEQ ID NO 153
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 153
aagggcttca tggagttctg                                              20

<210> SEQ ID NO 154
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 154
catgtccttg aagggcttca                                              20

<210> SEQ ID NO 155
<211> LENGTH: 20
<212> TYPE: DNA
<213> ORGANISM: Artificial Sequence
<220> FEATURE:

<223> OTHER INFORMATION: Oligomeric Compound

<400> SEQUENCE: 155
cgccagcttt aagagacgct                                        20

<210> SEQ ID NO 156
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 156
gctctgccac agcattgaga                                        20

<210> SEQ ID NO 157
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 157
tagaactcgc ggtctccaaa                                        20

<210> SEQ ID NO 158
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 158
ggtgacagac tcagcattcc                                        20

<210> SEQ ID NO 159
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 159
gatattccag ttctgccaaa                                        20

<210> SEQ ID NO 160
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 160
tgtctgatgc accacttgtg                                        20

<210> SEQ ID NO 161
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 161 agacccagt cctggccatc                                         20

<210> SEQ ID NO 162

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 162
tactcatgaa agaaagctga                                                  20

<210> SEQ ID NO 163
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 163
cattgctgtg aatgcccaaa                                                  20

<210> SEQ ID NO 164
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 164
acaatccagg ccagtgggac                                                  20

<210> SEQ ID NO 165
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 165
tgcattgcca tagttccctt                                                  20

<210> SEQ ID NO 166
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 166
gcccaatgat gagtgtcacc                                                  20

<210> SEQ ID NO 167
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 167
gtagtcgtgg acatacatga                                                  20

<210> SEQ ID NO 168
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 168
```
ttggcagtag ctcatgcccc                                              20

<210> SEQ ID NO 169
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 169
ctggcctttg gcagtagctc                                              20

<210> SEQ ID NO 170
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 170
cctccagaac tccaggccca                                              20

<210> SEQ ID NO 171
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 171
atccccaaga gcaggagtag                                              20

<210> SEQ ID NO 172
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 172
cccagcactg gctcaaccag                                              20

<210> SEQ ID NO 173
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 173
ttgatatcct aagcccctgg                                              20

<210> SEQ ID NO 174
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 174
tttttttttt ttagatagct                                              20